(12) United States Patent
Ferrari et al.

(10) Patent No.: US 6,811,770 B2
(45) Date of Patent: Nov. 2, 2004

(54) TWO-COAT MAKE-UP PROCESS AND A MAKE-UP KIT CONTAINING FIRST AND SECOND COMPOSITIONS

(75) Inventors: Veronique Ferrari, Maisons-Alfort (FR); CAroline Lebre, Thiais (FR); Pascal Arnaud, L'Hay les Roses (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/118,949

(22) Filed: Apr. 10, 2002

(65) Prior Publication Data

US 2003/0068344 A1 Apr. 10, 2003

Related U.S. Application Data

(60) Provisional application No. 60/293,980, filed on May 30, 2001.

(30) Foreign Application Priority Data

Apr. 10, 2001 (FR) .............................................. 01 04940
Feb. 6, 2002 (FR) .............................................. 02 01444

(51) Int. Cl.$^7$ .............................................. A61K 7/025
(52) U.S. Cl. .............................. 424/64; 424/61; 424/53; 424/69; 424/70.7; 424/401
(58) Field of Search ............................ 424/401, 61, 69, 424/63, 64, 70.7

(56) References Cited

U.S. PATENT DOCUMENTS

6,001,374 A    12/1999  Nichols

FOREIGN PATENT DOCUMENTS

EP    0 908 175 A1    4/1999

*Primary Examiner*—Jyothsna Venkat
(74) *Attorney, Agent, or Firm*—Oblon, Spivak, McClelland, Maier & Neustadt, P.C.

(57) ABSTRACT

A process for cosmetically making-up the skin and/or the lips and/or integuments of a human being, which comprises:
  applying to the skin, the lips and/or integuments a first coat of a first composition comprising, in a first physiologically acceptable medium, dispersed polymer particles surface-stabilized with a stabilizer in a liquid phase;
  permitting the first coat to dry; and then
  applying over all or a part of the first coat, a second coat of a second composition comprising, in a second physiologically acceptable medium, a silicone-based and/or fluoro-based liquid phase.

130 Claims, No Drawings

TWO-COAT MAKE-UP PROCESS AND A MAKE-UP KIT CONTAINING FIRST AND SECOND COMPOSITIONS

CROSS REFERENCE TO RELATED APPLICATION

The present application claims priority to provisional application Ser. No. 60/293,980, filed May 30, 2001.

BACKGROUND OF THE INVENTION

1. Field of the Invention

The present invention relates to a novel cosmetic two-coat makeup process for the skin and/or the lips and/or integuments by applying successively to human skin either of the face or the body, to the lower and upper eyelids of human beings, to the lips and to integuments such as the nails, the eyebrows, the eyelashes or the hair, at least one first and one second composition. The invention also relates to a make-up kit containing the first and second compositions.

Each of the compositions may be a free or compacted powder, a foundation, a face powder, an eyeshadow, a concealer product, a blusher, a lipstick, a lip balm, a lip gloss, a lip pencil, an eye pencil, a mascara, an eyeliner, a nail varnish or a body makeup or skin-coloring product.

2. Description of the Background

Make-up compositions for the skin or the lips of human beings, such as foundations or lipsticks, generally contain fatty phases such as waxes and oils, pigments and/or fillers and optionally additives, for instance cosmetic or dermatological active agents. They may also contain "pasty" compounds of soft consistency for obtaining colored or uncolored pastes, to be applied with a brush.

The known compounds have a tendency to migrate, that is to say to travel over time in the folds of the wrinkles and fine lines of the skin which especially surround the lips and the eyes, resulting in an unattractive effect. This migration is often mentioned by women as a major defect of standard lipsticks and eyeshadows. The term "migration" means a running of the composition and in particular of the color beyond the initial line of the make-up. In addition, these compositions have poor staying power over time, in particular of the color. This poor staying power is characterized by a modification of the color (color change or fading) generally following an interaction with the sebum and sweat secreted by the skin in the case of foundations and face powders, or of an interaction with saliva in the case of lipsticks. This obliges the user to apply fresh make-up very regularly, which may constitute wasted time.

For several years, cosmetic research has focused on "transfer-resistant" make-up compositions for the lips and the skin, that is to say compositions which have the advantage of forming a deposit that does not become deposited, at least partly, on the surfaces of supports with which they come into contact (glass, clothing, cigarettes, fabrics, etc.).

The known transfer-resistant compositions are generally based on silicone resins and volatile silicone oils and although having improved properties as regards staying power, have the drawback of leaving on the skin and the lips, after the volatile silicone oils have evaporated off, a film that becomes uncomfortable over time (sensation of dryness and of tautness), which puts a certain number of women off this type of lipstick.

In addition, these compositions based on volatile silicone oils and silicone resins produce matte colored films. However, women are nowadays looking for products, especially for coloring the lips or the eyelids, that are glossy while at the same time having good staying power and being transfer-resistant.

In order to overcome these drawbacks, Applicant has envisaged the manufacture of make-up compositions containing dispersed polymer particles surface-stabilized with a stabilizer in a liquid fatty phase, as described in EP-A-0 930 060. However, these compositions do not make it possible to achieve a really glossy make-up effect, which is always desired by consumers.

Moreover, Japanese patent application JP-A-05 221 829 assigned to the company Kose proposes the use of a gel based on perfluoro materials, which is applied over a film of lipstick so as to prevent it from transferring onto other surfaces, the gel being incompatible with the film of lipstick.

Although the use of perfluoro oils ensures incompatibility between the gel and the film of lipstick and thus staying power and transfer-resistance properties, formulations of this type have the drawback of possessing poor cosmetic properties, because the film of lipstick becomes oily and is liable to migrate, which is unacceptable for consumers.

Moreover, patent application WO-A-97/17057 assigned to the company Procter & Gamble, describes a method for increasing staying power and transfer-resistance properties, by applying two compositions, one over the other. These two compositions satisfy the following physicochemical criteria:

global Hildebrand solubility parameters of less than 8.5 $(cal/cm^3)^{1/2}$ for the composition applied first, presence of oil whose calculated partition coefficient ClogP is at least equal to 13 for the topcoat.

However, the selection of this composition does not exclude the possibility of having the same constituents in the two compositions. Specifically, triglycerides, in particular sweet almond oil and olive oil, mentioned as satisfying the partition coefficient criteria, also have Hildebrand solubility parameters of less than 8.5 $(cal/cm^3)^{1/2}$ (Vaughan C. D. "Solubility effects in product, package, penetration and preservation", Cosmetics and Toiletries, vol. 103, pp. 47–69, 1988):

Sweet almond oil: 6.81 $(cal/cm^3)^{1/2}$.

Olive oil 7.87 $(cal/cm^3)^{1/2}$.

Consequently, there is a certain level of compatibility between the two coats, which does not make it possible to achieve entirely satisfactory staying power and transfer-resistance properties.

Finally, U.S. Pat. No. 6,001,374 from Nichols proposes a multilayer make-up system that consists in using a composition containing an alcohol-soluble and water-insoluble resin, which may be applied as a basecoat or as a topcoat, and which has the advantage of not leaving marks on the surface of a support placed in contact with the make-up, and of being resistant to water and to friction, while at the same time possessing a certain level of gloss. However, this composition contains a water-soluble alcohol, in particular ethanol, which is a compound that has an irritant, dehydrating nature on the skin and more particularly on the lips, and which is particularly uncomfortable when the skin or the lips are damaged. Furthermore, this composition requires the use of a particular make-up remover, which is not particularly practical.

SUMMARY OF THE INVENTION

Accordingly, one object of the present invention is to provide a process for preparing a make-up which, simultaneously, is transfer-resistant, does not migrate, has good staying power, is comfortable, does not have a dehydrating effect, is not greasy, and is glossy, this result not having been satisfactorily obtained in the past.

Briefly, this object and other objects of the present invention as hereinafter will become more readily apparent can be attained by a cosmetic make-up process for the skin and/or the lips and/or integuments of a human being, which comprises:

applying to the skin, the lips and/or integuments a first coat of a first composition comprising, in a first physiologically acceptable medium, dispersed polymer particles surface-stabilized with a stabilizer in a liquid phase;

permitting the first coat to dry; and then applying over all or a part of the first coat, a second coat of a second composition comprising, in a second physiologically acceptable medium, a silicone-based and/or fluoro-based liquid phase.

BRIEF DESCRIPTION OF THE PREFERRED EMBODIMENTS

It has now been found, surprisingly, that by applying to the skin, the lips and/or integuments a first composition comprising a first physiologically acceptable medium containing dispersed polymer particles surface-stabilized with a stabilizer in a liquid phase and then a second composition comprising, in a second physiologically acceptable medium, a silicone-based and/or fluoro-based liquid phase, a glossy two-coat make-up is obtained, which does not migrate and does not transfer, while at the same time being comfortable when applied and over time (does not dehydrate the skin or make it taut).

In particular, the process of the invention permits the deposition of continuous deposits that are not sticky, with good coverage while having a glossy appearance, that are adapted to the consumer's desire, that are migration-resistant, transfer-resistant and have good staying power, that are not greasy and do not dehydrate the skin or the lips onto which the compositions are applied, either during application or over time. The make-up obtained also has good stability properties and is uniform and attractive.

Furthermore, it has been found that the compositions used in the process of the invention possess the particularly advantageous qualities of spreading on and adhering to the skin, the lips, the eyelashes or mucous membranes, and also has a pleasant, creamy feel. The compositions also have the advantage of being easy to remove, especially with a standard make-up remover. Because of the properties of staying power, transfer resistance and migration resistance of the make-up which is prepared, combined with its glossy, comfortable and non-greasy appearance, this process is particularly suitable for making-up the lips.

The expression make-up process means a process which permits a color to be deposited onto a keratin material (the skin, the lips or integuments) of a human being by the application to the keratin material of products, such as lipsticks, face powders, eyeliners, foundations or self-tanning products, or semipermanent make-up products (tattoo).

The physiologically acceptable compositions of the process of the invention are packaged separately or together in the same packaging article or in two (or more) separate or distinct packaging articles. Preferably, these compositions are packaged separately and, advantageously, in separate or distinct packaging articles.

Advantageously, the compositions of the two-coat process of the invention are in the form of a foundation, a face powder, an eyeshadow, a lipstick, a colored make-up product especially having care properties, an eyeliner, a concealer product or a body make-up product (of the tattoo type).

An aspect of the invention is also a cosmetic composition for conducting the make-up process described above. This composition comprises, in a physiologically acceptable medium, dispersed polymer particles surface-stabilized with a stabilizer in a liquid phase and a rheological agent selected from olefin copolymers of controlled crystallization, and mixtures thereof. Preferably, the rheological agent is an ethylene/octene copolymer.

Another aspect of the invention is a make-up kit containing a first and a second composition, the first composition comprising, in a first physiologically acceptable medium, dispersed polymer particles surface-stabilized with a stabilizer in a liquid phase, and the second composition comprising, in a second physiologically acceptable medium, a silicone-based and/or fluoro-based liquid phase.

Preferably, the first and second compositions are packaged separately and are accompanied by suitable application means. These means may be fine brushes, coarse brushes, pens, pencils, felts, nibs, sponges and/or foams. Felts are preferably used.

According to the process of the invention, the first composition can constitute a basecoat applied to the keratin material, and the second composition a topcoat. However, it is possible to apply, under the first coat, an undercoat which may or may not have the constitution of the second composition. It is also possible to apply an overcoat onto the second coat, which may or may not have an identical constitution to that of the first coat. Preferably, the make-up prepared is a two-coat make-up. In particular, the basecoat is a foundation, a face powder, a lipstick, a lip gloss, an eyeliner or a body make-up product, and the topcoat is a protective or care product.

The two-coat make-up may be adapted to all make-up products for the skin, not only for the face but also for the scalp and the body of human beings, mucous membranes, for instance, the lips and the inner edge of the lower eyelids, and integuments, for instance the nails, the eyelashes, the hair, the eyebrows, or even body hairs. The second coat can form patterns, and can be applied with a pen, a pencil or any other instrument (sponge, finger, fine brush, coarse brush, feather, etc.). This make-up may also be applied to make-up accessories, for instance, false nails, false eyelashes, wigs or small or large patches adhering to the skin or the lips (of the beauty-spot type).

Yet another aspect of the invention is a made-up support comprising a first coat of a first composition comprising, in a first physiologically acceptable medium, dispersed polymer particles surface-stabilized with a stabilizer in a liquid phase and optionally a coloring agent, and a second coat of a second composition, applied over all or some of the first coat, comprising, in a second physiologically acceptable medium, a silicone-based and/or fluoro-based phase.

This support may in particular be a hairpiece such as a wig, false nails, false eyelashes or patches adhering to the skin or the lips (of the beauty-spot type).

The invention also relates to a cosmetic make-up process defined above for improving the comfort and/or gloss and/or transfer and/or migration, and/or staying power properties of the make-up on the skin and/or the lips and/or integuments of human beings.

First Composition

The first composition of the process of the invention comprises, in a first physiologically acceptable medium, dispersed polymer particles surface-stabilized with a stabilizer in a liquid phase (referred to hereinbelow as "polymer dispersion").

The expression "physiologically acceptable medium" means a nontoxic medium that may be applied to the skin, integuments or the lips of the face of human beings.

For the purposes of the invention, the expression "cosmetically acceptable" means a composition with a pleasant appearance, odor, taste and feel.

Polymer in Dispersion

According to the invention, the polymer is a solid that is insoluble in the liquid phase of the first composition even at its softening point, unlike a wax even of polymeric origin, which is soluble in a liquid organic phase (or fatty phase) at its melting point. It also allows the formation of a deposit, especially a homogeneous, continuous, film-forming deposit. The polymer material is also characterized by entanglement of the polymer chains. With a wax, even one obtained by polymerization, recrystallization of the wax occurs after melting in a liquid organic phase. This recrystallization is in particular responsible for the loss of the gloss of the composition.

In order to have optimum transfer-resistance properties, the amount of polymer is chosen as a function of the amount of dyestuffs and/or active agents and/or oils contained in the first composition. In practice, the amount of polymer may be greater than 2% by weight (of active material) relative to the total weight of the composition.

One advantage of using a dispersion of polymer particles in a composition of the invention is that these particles remain in the form of elementary particles, without forming aggregates, in the liquid phase. Another advantage of the polymer dispersion is the possibility of obtaining very fluid compositions (of the order of 130 centipoises), even in the presence of a high content of polymer.

Yet another advantage of such a polymer dispersion is that it is possible to calibrate as desired the size of the polymer particles, and to modify their size "polydispersity" during the synthesis. It is thus possible to obtain particles of very small size, which are invisible to the naked eye when they are in the composition and when they are applied to the skin, the lips or integuments.

Another advantage of the polymer dispersion of the composition of the process of the invention is the possibility of varying the glass transition temperature (Tg) of the polymer or of the polymer system (polymer plus additive of the plasticizer type), and thus to go from a hard polymer to a more or less soft polymer, which allows the mechanical properties of the composition to be adjusted as a function of the intended application and in particular of the film applied.

The first composition of the process of the invention thus advantageously comprises at least one stable dispersion of generally spherical polymer particles of one or more polymers, in a physiologically acceptable liquid phase. These dispersions may especially be in the form of polymer nanoparticles in stable dispersion in said liquid phase. The nanoparticles preferably have a mean size ranging from 5 to 800 nm and better still from 50 to 500 nm. However, it is possible to prepare polymer particles ranging up to 1 μm in size.

Preferably, the polymer particles in dispersion are insoluble in water-soluble alcohols, for example such as ethanol.

The polymers in dispersion that may be used in the first composition of the invention preferably have a molecular weight ranging from about 2,000 to 10,000,000 and a Tg ranging from −100° C. to 300° C., better still from −50° C. to 100° C. and preferably from −10° C. to 50° C.

When the polymer has a glass transition temperature that is too high for the desired use, a plasticizer may be combined therewith so as to lower the temperature of the mixture used. The plasticizer may be selected from the plasticizers usually used in the field of application, and especially from compounds that are capable of being solvents for the polymer. Coalescers may also be used so as to help the polymer to form a continuous and uniform deposit.

The coalescers or plasticizers that may be used in the invention are especially those described in FR-A-2 782 917.

It is possible to use film-forming polymers, preferably having a low Tg, of less than or equal to the temperature of the skin and especially less than or equal to 40° C.

Preferably, the polymer used is film-forming, that is to say that it is capable, by itself or in combination with a plasticizer, of forming an isolable film. However, it is possible to use a non-film-forming polymer.

The expression "non-film-forming polymer" means a polymer not capable by itself of forming an isolable film. This polymer makes it possible, in combination with a nonvolatile compound of the oil type, to form a continuous and uniform deposit on the skin and/or the lips.

Among the film-forming polymers that may be mentioned are free-radical, acrylic or vinyl homopolymers or copolymers, preferably with a Tg of less than or equal to 40° C. and especially ranging from −10° C. to 30° C., used alone or as a mixture.

Among the non-film-forming polymers that may be mentioned are free-radical, vinyl or acrylic homopolymers or copolymers, that are optionally crosslinked, preferably with a Tg of greater than 40° C. and especially ranging from 45° C. to 150° C., used alone or as a mixture.

The expression "free-radical polymer" means a polymer obtained by polymerization of monomers containing unsaturation, especially ethylenic unsaturation, each monomer being capable of homopolymerizing (unlike polycondensates). The free-radical polymers may especially be vinyl polymers or copolymers, especially acrylic polymers.

The vinyl polymers may result from the polymerization of ethylenically unsaturated monomers containing at least one acid group and/or esters of these acidic monomers and/or amides of these acids.

Monomers bearing an acidic group that may be used include $\alpha,\beta$-ethylenic unsaturated carboxylic acids such as acrylic acid, methacrylic acid, crotonic acid, maleic acid and itaconic acid. (Meth)acrylic acid and crotonic acid are preferably used, and more preferably (meth)acrylic acid.

The esters of acidic monomers are advantageously selected from among (meth)acrylic acid esters (also known as (meth)acrylates), for instance alkyl (meth)acrylates, in particular, $C_1$–$C_{20}$, preferably $C_1$–$C_8$ alkyl esters, aryl (meth)acrylates, in particular, $C_6$–$C_{10}$ aryl esters, hydroxyalkyl (meth)acrylates, in particular, $C_2$–$C_6$ hydroxyalkyl esters. Suitable alkyl (meth)acrylates include methyl, ethyl, butyl, isobutyl, 2-ethylhexyl and lauryl (meth)acrylate. Suitable hydroxyalkyl (meth)acrylates include hydroxyethyl (meth)acrylate and 2-hydroxypropyl (meth)acrylate. Suitable aryl (meth)acrylates include benzyl or phenyl acrylate.

The (meth)acrylic acid esters that are particularly preferred are the alkyl (meth)acrylates.

Free-radical polymers that are preferably used include copolymers of (meth)acrylic acid and of an alkyl (meth)acrylate, especially of a $C_1$–$C_4$ alkyl (meth)acrylate. More preferably, methyl acrylates optionally copolymerized with acrylic acid may be used.

Suitable amides of acidic monomers include (meth) acrylamides, and especially N-alkyl(meth)acrylamides, in particular of a $N-C_2-C_{12}$ alkyl (meth)acrylamides, such as N-ethylacrylamide, N-t-butylacrylamide and N-octylacrylamide; $N-di(C_1-C_4)$alkyl-(meth)acrylamides.

The vinyl polymers may also result from the polymerization of ethylenically unsaturated monomers containing at least one amine group, in free form or in partially or totally neutralized form, or alternatively in partially or totally quaternized form. Such monomers may be, for example, dimethylaminoethyl (meth)acrylate, dimethylaminoethylmethacrylamide, vinylamine, vinylpyridine or diallyldimethylammonium chloride.

The vinyl polymers may also be derived by the homopolymerization or copolymerization of at least one monomer selected from vinyl esters and styrene monomers. In particular, these monomers may be polymerized with acidic monomers and/or esters thereof and/or amides thereof, such as those mentioned above. Suitable examples of vinyl esters include vinyl acetate, vinyl propionate, vinyl neodecanoate, vinyl pivalate, vinyl benzoate and vinyl t-butylbenzoate. Suitable styrene monomers include styrene and α-methylstyrene.

The list of monomers given is not limiting and it is possible to use any monomer known to those skilled in the art that fall within the categories of acrylic and vinyl monomers (including monomers modified with a silicone chain).

Suitable examples of other vinyl monomers that may be used include:

N-vinylpyrrolidone, vinylcaprolactam, vinyl-N-$(C_1-C_6)$ alkylpyrroles, vinyloxazoles, vinylthiazoles, vinylpyrimidines and vinylimidazoles, olefins such as ethylene, propylene, butylene, isoprene and butadiene.

The vinyl polymer may be crosslinked with one or more difunctional monomers especially comprising at least two ethylenic sites of unsaturations, such as ethylene glycol dimethacrylate or diallyl phthalate.

In a non-limiting manner, the polymers in dispersion of the invention may be selected from among the following polymers or copolymers: polyurethanes, polyurethane-acrylics, polyureas, polyurea-polyurethanes, polyester-polyurethanes, polyether-polyurethanes, polyesters, polyesteramides, alkyd fatty-chain polyesters; acrylic and/or vinyl polymers or copolymers; acrylic-silicone copolymers; polyacrylamides; silicone polymers, for instance silicone acrylics or polyurethanes, fluoro polymers, and mixtures thereof.

The content of polymer(s) in dispersion in the liquid phase, as solids, may range from 2% to 40% of the weight of the composition, preferably from 5% to 30% and better still from 8% to 20%. When the polymer particles in dispersion are surface-stabilized with a stabilizer that is solid at room temperature, the amount of solids in the dispersion represents the total amount of polymer+stabilizer, given that the amount of polymer cannot be less than 2%.

Liquid Phase of the First Composition

In describing the present invention, the expression "liquid phase" means any aqueous or organic phase that is liquid at room temperature (25° C.) and atmospheric pressure (760 mmHg).

The expression "aqueous phase" means a medium containing water and optionally water-miscible liquid compounds, for instance polyols containing from 2 to 6 hydroxyl groups and from 2 to 8 carbon atoms, for instance glycerol, diglycerol, ethylene glycol and sorbitol, and mixtures thereof.

The aqueous phase may represent from 5% to 98% of the total weight of the composition, preferably from 20% to 85% and better still from 30% to 70% of the total weight of the composition.

Suitable aqueous polymer dispersions that may be used in the present invention include the dispersions described in U.S. Pat. Nos. 5,972,354, 6,010,686, EP-A-0 875 242, EP-A-0 875 243 and FR-A-2 782 917.

The aqueous polymer dispersions of the invention are prepared by a person skilled in the art on the basis of his general knowledge, especially by emulsion polymerization in the presence of an emulsifier in water or by dispersing the preformed polymer in water.

Preferably, a polyurethane or an acrylic polymer in aqueous dispersion, which is commercially available, is used, and especially an acrylic/styrene polymer sold by the company Zeneca under the name Neocryl A-1070.

After evaporation of the water on contact with the skin, the lips or integuments, a continuous and homogeneous polymer deposit is obtained.

The liquid phase is preferably a liquid organic phase.

The expression "liquid organic phase" according to the invention means any non-aqueous medium that is liquid at room temperature (25° C.) and atmospheric pressure (760 mm Hg), composed of one or more fatty substances that are liquid at room temperature, also known as oils. This liquid organic phase is macroscopically homogeneous i.e., homogeneous to the naked eye. This organic phase may contain a volatile liquid organic phase and/or a nonvolatile organic phase.

The expression "nonvolatile organic phase" means any medium capable of remaining on the skin or the lips for several hours. A nonvolatile liquid organic phase in particular has a nonzero vapor pressure at room temperature and atmospheric pressure, of less than 0.02 mm Hg (2.66 Pa) and better still less than $10^{-3}$ mm Hg (0.13 Pa).

The expression "volatile organic phase" means any non-aqueous medium that is capable of evaporating from the skin or the lips in less than one hour at room temperature and atmospheric pressure. This volatile phase especially comprises oils with a vapor pressure, at room temperature (25° C.) and atmospheric pressure (760 mm Hg) ranging from 0.02 to 300 mm Hg (2.66 Pa to 40,000 Pa) and preferably from 0.05 to 300 mm Hg (6.65 Pa to 40,000 Pa).

Advantageously, the volatile organic phase contains one or more volatile oils with a flashpoint ranging from 30° C. to 102° C.

The liquid fatty substances or oils of which the organic liquid phase is composed are selected from oils of mineral, animal, plant or synthetic origin, carbon-based oils, hydrocarbon-based oils, fluoro oils and/or silicone oils, alone or as a mixture provided that they form a macroscopically stable and homogeneous mixture and provided that they are suitable for the intended use.

The expression "hydrocarbon-based oil" means oils predominantly containing carbon atoms and hydrogen atoms and in particular alkyl or alkenyl chains, for instance alkanes or alkenes, but also oils with an alkyl or alkenyl chain comprising one or more alcohol, ether, ester or carboxylic acid groups.

The total liquid organic phase of the first composition may range from 5% to 98% of the total weight of the composition, preferably from 20% to 85%. Advantageously, the amount represents at least 30% of the total weight of the composition.

Suitable volatile organic oils that may be used include hydrocarbon-based oils of mineral or synthetic origin such as linear or branched hydrocarbons, for instance liquid paraffin and its derivatives, liquid petroleum jelly, polydecenes, hydrogenated polyisobutene such as Parleam sold by the company Nippon Oil Fats, squalane of synthetic or plant origin; oils of animal origin, such as mink oil, turtle oil or perhydrosqualene; hydrocarbon-based oils of plant origin with a high triglyceride content consisting of fatty acid esters of glycerol, the fatty acids of which may have varied chain lengths, said chains possibly being linear or branched, and saturated or unsaturated, for instance sweet almond oil, beauty-leaf oil, palm oil, grapeseed oil, sesame oil, arara oil, rapeseed oil, sunflower oil, cottonseed oil, apricot oil, castor oil, alfalfa oil, marrow oil, blackcurrant oil, macadamia oil, musk rose oil, hazelnut oil, avocado oil, jojoba oil, olive oil or cereal germ oil (from corn, wheat, barley or rye); fatty acid esters and especially esters of lanolic acid, of oleic acid, of lauric acid or of stearic acid; synthetic esters of formula $R_1COOR_2$ in which $R_1$ represents the linear or branched higher fatty acid residue containing from 7 to 40 carbon atoms and $R_2$ represents a branched hydrocarbon-based chain containing from 3 to 40 carbon atoms, such as, for example, purcellin oil (cetostearyl octanoate), isononyl isononanoate, $C_{12}$ to $C_{15}$ alkyl benzoate, 2-ethylhexyl palmitate, octanoates, decanoates or ricinoleates of alcohols or of polyalcohols, isopropyl myristate, isopropyl palmitate, butyl stearate, hexyl laurate, diisopropyl adipate, 2-ethylhexyl palmitate, 2-hexyldecyl laurate, 2-octyldecyl palmitate, 2-octyldodecyl myristate, 2-diethylhexyl succinate, diisostearyl malate, or glyceryl or diglyceryl triisostearate; hydroxylated esters, for instance isostearyl lactate; pentaerythritol esters; $C_8$–$C_{26}$ higher fatty acids such as oleic acid, linoleic acid, linolenic acid or isostearic acid; $C_8$–$C_{26}$ higher fatty alcohols such as oleyl alcohol, linoleyl alcohol, linolenyl alcohol, isostearyl alcohol or octyldodecanol; synthetic ethers containing at least 7 carbon atoms, silicone oils such as polydimethylsiloxanes (PDMS) that are liquid at room temperature, linear, and optionally phenylated, such as phenyltrimethicones, phenyltrimethylsiloxydiphenylsiloxanes, diphenyldimethicones, diphenylmethyldiphenyltrisiloxanes, liquid 2-phenylethyl trimethylsiloxysilicates, optionally substituted with aliphatic and/or aromatic groups, for instance alkyl, alkoxy or phenyl groups that are pendent and/or at the end of a silicone chain, these groups containing from 2 to 24 carbon atoms and being optionally fluorinated, or with functional groups such as hydroxyl, thiol and/or amine groups; polysiloxanes modified with fatty acids, with fatty alcohols or with polyoxyalkylenes, for instance dimethicone copolyols or alkylmethicone copolyols; liquid fluorosilicones; or caprylic/capric acid triglycerides, for instance those sold by the company Stearineries Dubois or those sold under the names Miglyol 810, 812 and 818 by the company Dynamit Nobel; and mixtures thereof.

Advantageously, the liquid organic phase may contain one or more organic oils that are volatile at room temperature, for instance volatile cosmetic oils. These oils are favorable toward the production of a deposit with good staying power that is transfer-resistant. After evaporating these oils, a flexible film-forming deposit that is not sticky on the skin or the lips remains. These volatile oils also make it easier to apply the composition to the skin, the lips and integuments. They may be hydrocarbon-based, silicone-based and/or fluoro-based oils and may optionally comprise alkyl or alkoxy groups that are pendent or at the end of a silicone chain.

Suitable volatile organic oils that may be used in the invention include linear or cyclic silicone oils with a viscosity at room temperature of less than 8 mm²/s and especially containing from 2 to 7 silicon atoms, these silicones optionally comprising alkyl or alkoxy groups containing from 1 to 10 carbon atoms. Suitable volatile silicone oils that may be used in the invention include octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Suitable other volatile oils that may be used in the invention include hydrocarbon-based volatile oils containing from 8 to 16 carbon atoms and mixtures thereof, and especially $C_8$–$C_{16}$ branched alkanes, for instance $C_8$–$C_{16}$ isoalkanes (also known as isoparaffins), isododecane, isodecane, isohexadecane and, for example, the oils sold under the trade names "Isopars" or "Permethyls", and $C_8$–$C_{16}$ branched esters, for instance isohexyl neopentanoate, and mixtures thereof.

Advantageously, the volatile organic oil(s) represent(s) from 20% to 90%, preferably from 30% to 80% and better still from 40% to 70% of the total weight of the first composition.

When the liquid organic phase of the first composition contains a volatile oil, this first composition preferably forms the basecoat of the two-coat makeup.

The dispersion of polymer in liquid organic phase may be prepared as described in EP-A-0 749 747. The polymerization may be conducted in a dispersion, that is to say by precipitation of the polymer during formation, with protection of the particles formed with a stabilizer. In this case, a mixture comprising the initial monomers and also a free-radical initiator is prepared, and this mixture is then dissolved in a medium that is referred to in the rest of the present description as the "organic synthesis medium". When the liquid phase is organic and contains a nonvolatile oil, the polymerization may be conducted in an apolar organic medium (synthesis medium), followed by addition of the nonvolatile oil, which must be miscible with said synthesis medium, and selective distillation of the synthesis medium.

A synthesis medium is thus selected such that the initial monomers, and the free-radical initiator, are soluble therein, and the polymer particles obtained are insoluble therein, so that they precipitate during their formation. In particular, the synthesis medium can be selected from alkanes including heptane, isododecane and cyclohexane.

When the liquid phase of the first composition is a volatile oil, the polymerization may be conducted directly in the oil, which thus also acts as the synthesis medium. The monomers must also be soluble therein, as must the free-radical initiator, and the polymer prepared must be insoluble therein.

The monomers are preferably present in the synthesis medium, before polymerization, in an amount ranging from 5–20% by weight of the reaction mixture. The total amount of monomers may be present in the medium before the start of the reaction, or a portion of the monomers may be added gradually as the polymerization reaction proceeds.

The free-radical initiator may especially be azobisisobutyronitrile or tert-butylperoxy-2-ethyl hexanoate.

Stabilizer

Advantageously, the polymerization of the polymer in the organic synthesis medium is conducted in the presence of a stabilizer of polymer type.

The polymer particles in organic medium are surface-stabilized, gradually as the polymerization proceeds by means of a stabilizer which may be a block polymer, a grafted polymer and/or random polymer, alone or as a mixture. The stabilization may be conducted by any known means, and in particular by directly adding the block polymer, grafted polymer and/or random polymer during the polymerization.

The stabilizer is preferably also incorporated in the mixture before polymerization. However, it is also possible to add it continuously to the polymerization medium, especially when the monomers are also added continuously.

2–30% by weight of stabilizer may be used relative to the initial monomer mixture, preferably 5–20% by weight.

When a grafted and/or block polymer is used as stabilizer, the solvent employed in synthesis is selected such that at least some of the grafts or blocks of the polymer-stabilizer are soluble in the solvent, the other part of the grafts or blocks not being soluble therein. The polymer-stabilizer used during the polymerization must be soluble, or dispersible, in the synthesis solvent. Furthermore, a stabilizer whose insoluble grafts or blocks have a certain affinity for the polymer formed during the polymerization is preferably employed.

Suitable graft polymers include silicone polymers having grafts of a hydrocarbon-based chain; hydrocarbon-based polymers having grafts of a silicone chain.

Graft copolymers having, for example, an insoluble backbone of the polyacrylic type with soluble grafts of the poly(12-hydroxystearic acid) type are also suitable.

It is thus possible to use grafted-block or block copolymers comprising at least one block of the polyorganosiloxane type and at least one block of a free-radical monomer, such as grafted copolymers of the acrylic/silicone type which may be used especially when the synthesis medium and then the organic liquid phase of the first composition contains a silicone phase.

It is also possible to use graft-block or block copolymers comprising at least one block of the polyorganosiloxane type and at least one block of a polyether. The polyorganopolysiloxane block may especially be a polydimethylsiloxane or a poly($C_2$–$C_{18}$)alkyhnethylsiloxane; the polyether block may be a poly($C_2$–$C_{18}$ alkylene), in particular polyoxyethylene and/or polyoxypropylene. In particular, dimethicone copolyols or ($C_2$–$C_{18}$)alkyldimethicone copolyols may be used, such as those sold under the name "Dow Corning 3225C" by the company Dow Corning, and lauryl methicones such as those sold under the name "Dow Corning Q2-5200" by the company Dow Corning.

Suitable grafted-block or block copolymers which can be used include copolymers comprising at least one block resulting from the polymerization of at least one ethylenic monomer, containing one or more optionally conjugated ethylenic bonds, such as ethylene, or dienes such as butadiene or isoprene, and of at least one block of a vinyl, or preferably styrene, polymer. When the ethylenic monomer comprises several optionally conjugated ethylenic bonds, the residual sites of ethylenic unsaturation after the polymerization are generally hydrogenated. Thus, in a known manner, the polymerization of isoprene leads, after hydrogenation, to the formation of ethylene-propylene blocks, and the polymerization of butadiene leads, after hydrogenation, to the formation of ethylene-butylene blocks. Suitable such polymers include block copolymers, in particular, of the "diblock" or "triblock" type such as polystyrene/polyisoprene (SI) or polystyrene/polybutadiene (SB), such as those sold under the name 'Luvitol HSB' by BASF, of the polystyrene/copoly(ethylene-propylene) (SEP) type, such as those sold under the name 'Kraton' by Shell Chemical Co. or alternatively of the polystyrene/copoly (ethylene-butylene) (SEB) type. In particular, Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS) or Kraton D-1107 (SIS) may be used. Polymers are generally known as hydrogenated or non-hydrogenated diene copolymers.

Gelled Permethyl 99A-750, 99A-753-59 and 99A-753-58 (mixture of triblock and starburst polymer), Versagel 5960 from Penreco (triblock+starburst polymer); OS129880, OS129881 and OS84383 from Lubrizol (styrene/methacrylate copolymer) may also be used.

Suitable graft-block or block copolymers comprising at least one block resulting from the polymerization of at least one ethylenic monomer with one or more ethylenic bonds, and of at least one block of an acrylic polymer include poly(methyl methacrylate)/polyisobutylene diblock or triblock copolymers or graft copolymers with a poly(methyl methacrylate) backbone and with polyisobutylene grafts.

Suitable graft-block or block copolymers comprising at least one block resulting from the polymerization of at least one ethylenic monomer with one or more ethylenic bonds and of at least one block of a polyether such as a $C_2$–$C_{18}$ polyalkylene, in particular polyethylenated and/or polyoxypropylenated include polyoxyethylene/polybutadiene or polyoxyethylene/polyisobutylene diblock or triblock copolymers.

When a random polymer is used as stabilizer, it is selected on the basis that it has a sufficient amount of groups that make it soluble in the intended organic synthesis medium.

Copolymers based on acrylate or methacrylate esters derived from $C_1$–$C_4$-alcohols, and acrylate or methacrylate esters derived from $C_8$–$C_{30}$-alcohols may thus be used. Suitable such esters in particular include stearyl methacrylate/methyl methacrylate copolymer.

When the synthesis medium is apolar, the stabilizer preferably selected is a polymer which covers the particles as completely as possible, several stabilizing-polymer chains then becoming adsorbed on a polymer particle obtained by polymerization.

In this case, the stabilizer preferably used is either a graft polymer or a block polymer, so as to have better interfacial activity. The reason for this is that the blocks or grafts that are insoluble in the synthesis solvent provide more voluminous coverage at the surface of the particles.

When the liquid synthesis medium comprises at least one silicone oil, the stabilizer is preferably selected from the group consisting of graft-block or block copolymers comprising at least one block of the polyorganosiloxane type and at least one block of a free-radical polymer or of a polyether or a polyester, such as polyoxypropylenated and/or polyoxyethylenated blocks.

When the organic liquid phase does not comprise a silicone oil, the stabilizer is preferably selected from the group consisting of:
  (a) graft-block or block copolymers comprising at least one block of the polyorganosiloxane type and at least one block of a free-radical polymer or of a polyether or a polyester,
  (b) copolymers of acrylate or methacrylate esters derived from $C_1$–$C_4$-alcohols and of acrylate or methacrylate esters derived from $C_8$–$C_{30}$-alcohols,
  (c) graft-block or block copolymers comprising at least one block resulting from the polymerization of at least one ethylenic monomer containing conjugated ethylenic bonds, and at least one block of a vinyl or acrylic polymer or of a polyether or a polyester, or mixtures thereof.

Diblock polymers are preferably used as stabilizer.

Rheological Agent

Advantageously, the first composition contains one or more rheological agents for structuring and/or gelling its physiologically acceptable medium.

The rheological agent or agents is(are) agents capable of thickening and/or gelling the composition. They may be present in an amount that is effective to increase the viscosity of the composition until a solid gel is obtained, that is to say a product that does not run under its own weight, or even a stick.

The rheological agent especially is present in an amount ranging from 0.1% to 50% of the total weight of the first composition and better still from 1% to 25%.

This rheological agent is advantageously chosen from lipophilic gelling agents, waxes and fillers, and mixtures thereof.

Lipophilic Gelling Agent

According to one preferred embodiment of the invention, the first composition contains a liquid organic phase; it may thus comprise, as a rheological agent, an agent which gels the liquid organic phase.

Suitable organic-phase gelling agents optionally include modified clays, for instance, hectorites modified with an ammonium chloride of a $C_{10}$ to $C_{22}$-fatty acid, for instance hectorite modified with distearyldimethylammonium chloride; fumed silica optionally hydrophobically surface-treated, with a particle size of less than 1 µm; partially or totally crosslinked elastomeric polyorganosiloxanes, of three-dimensional structure, such as those sold under the names KSG6, KSG16, and KSG18 from Shin-Etsu, Trefil E-505C or Trefil E-506C from Dow-Corning, Gransil SR-CYC, SR DMF10, SR-DC556, SR 5CYC gel, SR DMF 10 gel and SR DC 556 gel from Grant Industries, SF 1204 and JK 113 from General Electric; galactomannans comprising from one to six and better from two to four hydroxyl groups per saccharide, substituted with a saturated or unsaturated alkyl chain, for instance guar gum alkylated with $C_1$ to $C_6$ and better still $C_1$ to $C_3$ alkyl chains, and more particularly ethylated guar having a degree of substitution of 2 to 3, such as the product sold by the company Aqualon under the name N-Hance-AG; ethylcellulose, for instance the products sold under the name Ethocel by Dow Chemical; gums, especially silicone gums, for instance PDMSs having a viscosity>100 000 centistokes.

The rheological agent may also be selected from ethylene homopolymers or copolymers with a weight-average molecular weight ranging from 300 to 500,000, better still from 500 to 100,000.

Preferably, the gelling agent is selected from olefin copolymers of controlled crystallization, and mixtures thereof, as described in Applicants patent application EP-A-1 034 776 such as, for example, the ethylene/octene copolymer sold under the name Engage 8400 by Dupont de Nemours. This type of gelling agent gives a film of a first composition and, consequently, a final make-up that possesses particularly advantageous staying power and transfer-resistance properties.

The rheological agent or agents is(are) used, for example, at concentrations ranging from 0.5% to 20%, better still from 1% to 10% of the total weight of the first composition.

Wax

The rheological agent may also comprise a wax selected from waxes that are solid at room temperature, such as hydrocarbon-based waxes, for instance optionally modified beeswax, carnauba wax, candelilla wax, ouricurry wax, Japan wax, cork fiber wax or sugar cane wax, paraffin wax, lignite wax, microcrystalline wax, lanolin wax, montan wax, ozokerites, polyethylene wax or ethylene copolymer wax, the waxes obtained by Fischer-Tropsch synthesis, hydrogenated oils, fatty esters and glycerides that are solid at 25° C. Silicone waxes may also be used, which include alkyl, alkoxy and/or esters of polymethylsiloxane. The waxes may be in the form of stable dispersions of colloidal wax particles as may be prepared according to known methods, such as those of "Microemulsions Theory and Practice", L. M. Prince Ed., Academic Press (1977), pages 21–32. Preferably, the waxes have a melting point at least equal to 45° C.

The waxes may be present in an amount ranging from 0.1% to 50% by weight in the first composition and better still from 3% to 25%, so as not to excessively reduce the gloss of this composition and of the film deposited on the lips and/or the skin.

Filler

The rheological agent may furthermore comprise a filler. The term "filler" means any colorless or white particle selected from mineral or organic, lamellar, spherical or oblong fillers, that are chemically inert in the first composition. Suitable fillers include talc, mica, silica, kaolin, polyamide powders, for instance Nylon® powder (Orgasol® from Atochem), poly-β-alanine powders and polyethylene powders, powders of tetrafluoroethylene polymers (Teflon®), lauroyllysine, starch, boron nitride, hollow polymer microspheres such as those of polyvinylidene chloride/acrylonitrile, such as Expancel® (Nobel Industrie), acrylic polymer particles, especially of acrylic acid copolymer, for instance Polytrap® (Dow Corning) and silicone resin microbeads (for example Tospearls® from Toshiba), precipitated calcium carbonate, dicalcium phosphate, magnesium carbonate and magnesium hydrocarbonate, hydroxyapatite, hollow silica microspheres (Silica Beads® from Maprecos), glass or ceramic microcapsules, metal soaps derived from organic carboxylic acids containing from 8 to 22 carbon atoms, preferably from 12 to 18 carbon atoms, for example zinc stearate, magnesium stearate or lithium stearate, zinc laurate and magnesium myristate, and mixtures thereof. These fillers may or may not be surface-treated, especially to make them lipophilic.

Preferably, the fillers have a particle size of less than 50 µm and represent from 0.1% to 35%, preferably from 0.5% to 25% and better still from 1% to 15% of the total weight of the first composition, if they are present.

Second Composition

The second composition employed in the process of the invention comprises, in a physiologically acceptable medium, a silicone-based, fluoro-based or silicone-based and fluoro-based liquid phase.

According to one preferred embodiment of the invention, the silicone-based and/or fluoro-based liquid phase comprises a liquid phase that is nonvolatile at room temperature and atmospheric pressure.

The expression "nonvolatile liquid phase" means any medium capable of remaining on the skin or the lips for several hours. A nonvolatile liquid phase in particular has a vapor pressure at room temperature and atmospheric pressure that is not zero, of less than 0.02 mm Hg (2.66 Pa) and better still less than $10^{-3}$ mm Hg (0.13 Pa).

The nonvolatile liquid phase of the second composition advantageously contains at least one nonvolatile silicone oil and preferably a phenylsilicone oil.

The phenylsilicone oils that may be used in the present invention have a viscosity, measured at 25° C. and atmospheric pressure, ranging from 5 to 100,000 cSt and preferably from 5 to 10,000 cSt.

Suitable silicone oils include, for example, a phenyl trimethicone, a phenyl dimethicone, a phenyl trimethylsiloxydiphenylsiloxane, a diphenyl dimethicone, a diphenylmethyldiphenyltrisiloxane or a mixture of various phenylsilicone oils, and in particular may correspond to formula (A) below:

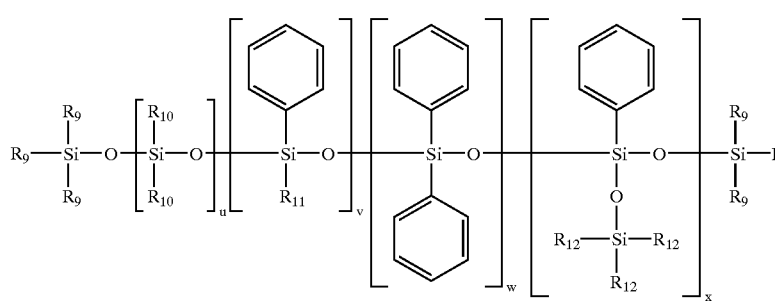

(A)

wherein $R_9$ and $R_{12}$ are each independently is a $C_1$–$C_{30}$ alkyl radical, an aryl radical or an aralkyl radical;

$R_{10}$ and $R_{11}$ are each independently a $C_1$–$C_{30}$-alkyl radical or an aralkyl radical, u, v, w and x are each independently integers ranging from 0 to 900, with the proviso that the sum v+w+x is other than 0 and that the sum u+v+w+x ranges from 1 to 900, in particular u+v+w+x ranges from 1 to 800.

Advantageously, $R_9$ is a $C_1$–$C_{20}$-alkyl radical, a phenyl radical or an aralkyl radical of the type R'—$C_6H_5$, R' being a $C_1$–$C_5$-alkyl, $R_{10}$ and $R_{11}$ are each independently a $C_1$–$C_{20}$-alkyl radical or an aralkyl radical of the type R'—$C_6H_5$, R' being a $C_1$–$C_5$-alkyl, and $R_{12}$ is a $C_1$–$C_{20}$-alkyl radical.

Preferably, $R_9$ is a methyl, ethyl, propyl, isopropyl, decyl, dodecyl or octadecyl radical or a phenyl, tolyl, benzyl or phenethyl radical, $R_{10}$ and $R_{11}$ are each independently a methyl, ethyl, propyl, isopropyl, decyl, dodecyl or octadecyl radical or a tolyl, benzyl or phenethyl radical, and $R_{12}$ is a methyl, ethyl, propyl, isopropyl, decyl, dodecyl or octadecyl radical.

According to one preferred embodiment of the invention, the silicone-based phase of the second composition contains a nonvolatile liquid phase which comprises a phenylsilicone oil with a viscosity of less than 500 cSt at 25° C., known as a "low-viscosity phenylsilicone oil", and a phenylsilicone oil with a viscosity at least equal to 500 cSt at 25° C., known as a "high-viscosity phenylsilicone oil". Advantageously, the low-viscosity phenylsilicone oil has a viscosity at 25° C. ranging, for example, from 5 to 499 cSt, preferably from 5 to 300 cSt and better still from 5 to 100 cSt, and the high-viscosity phenylsilicone oil has a viscosity at 25° C. ranging, for example, from 500 to 10,000 cSt, preferably from 600 to 5,000 cSt and better still from 600 to 3,000 cSt.

The use of low-viscosity and high-viscosity phenylsilicone oils as defined above makes it possible to obtain, after application to the skin, the lips and/or integuments, a film of composition that is particularly glossy, homogeneous and of good staying power.

Preferably, these low-viscosity and high-viscosity phenylsilicone oils satisfy formula (A). Preferably, the low-viscosity phenylsilicone oil satisfies formula (A) with the sum u+v+w+x ranging from 1 to 150, better still from 1 to 100 or even from 1 to 50, and the high-viscosity phenylsilicone oil satisfies formula (A) with the sum u+v+w+x ranging from 151 to 1,000, better still from 160 to 800, or even from 160 to 500.

In particular, the low-viscosity phenyl silicone oil satisfies formula (I) below:

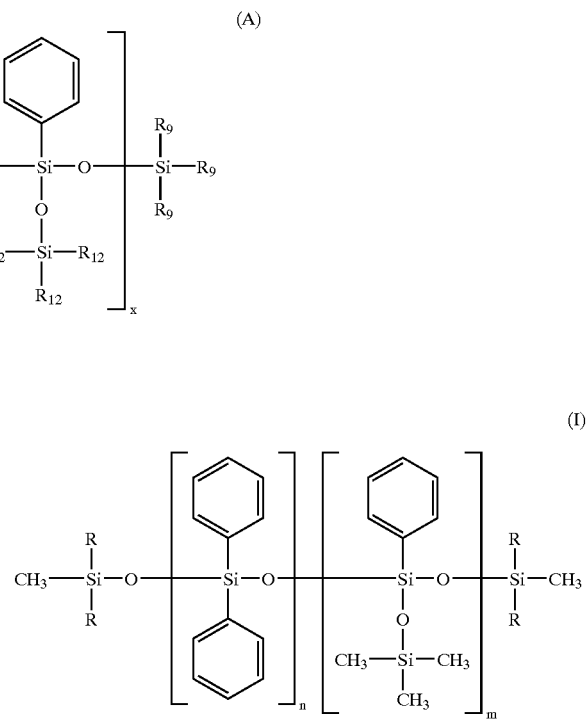

(I)

wherein:

R is a $C_1$–$C_{30}$-alkyl radical, an aryl radical or an aralkyl radical, n is an integer ranging from 0 to 100, better still, of less than 100, m is an integer ranging from 0 to 100, with the proviso that the sum m+n ranges from 1 to 100, better still, is less than 100.

Advantageously, R is a $C_1$–$C_{20}$-alkyl radical, a phenyl radical or an aralkyl radical of the type R'—$C_6H_5$, R' being a $C_1$–$C_5$-alkyl.

Preferably, R is a methyl, ethyl, propyl, isopropyl, decyl, dodecyl or octadecyl radical, or alternatively a phenyl, tolyl, benzyl or phenethyl radical. R is advantageously a methyl radical.

Suitable phenylsilicone oils include DC556 (22.5 cSt) or SF558 (10–20 cSt) from Dow Corning, Abil AV8853 (4–6 cSt) from Goldschmidt, Silbione 70 633 V 30 (28 cSt) from Rhône-Poulenc, 15 M 40 (50 to 100 cSt), or 15 M 50 (20 to 25 cSt) from PCR, SF 1550 (25 cSt) or PK 20 (20 cSt) from Bayer, Belsil PDM 200 (200 cSt) from Wacker and KF 53 (175 cSt), KF 54 (400 cSt) and KF 56 (14 cSt) from Shin-Etsu. Suitable high-viscosity phenylsilicone oils that may be used include 15 M 30 from PCR (500 cSt) and Belsil PDM 1000 (1000 cSt) from Wacker.

The values in parentheses represent the viscosities at 25° C.

The weight ratio of the low-viscosity phenylsilicone oil to the high-viscosity phenylsilicone oil can range, for example, from 70/30 to 30/70, better still from 60/40 to 40/60 and even better still from 55/45 to 45/55.

The nonvolatile liquid phase of the second composition may comprise at least one fluoro compound selected from fluorosilicone compounds, fluoro polyethers and/or fluoroalkanes.

Preferably, the fluorosilicone compound is selected from the compounds of formula (II) below:

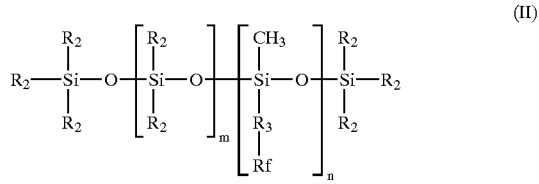

wherein:
- $R_3$ represents a linear or branched divalent alkyl group containing 1 to 6 carbon atoms, preferably a divalent methyl, ethyl, propyl or butyl group;
- Rf represents a fluoroalkyl radical, especially a perfluoroalkyl radical, containing 1 to 9 carbon atoms, preferably 1 to 4 carbon atoms;
- $R_2$ represent, independently of each other, a $C_1$–$C_{20}$-alkyl radical, a hydroxyl radical or a phenyl radical;
- m is selected from 0 to 150, preferably from 20 to 100; and
- n is selected from 1 to 300, preferably from 1 to 100.

Suitable fluorosilicone compounds of formula (II) include those sold by Shin-Etsu under the names "X22-819", "X22-820", "X22-821" and "X22-822" or "FL-100".

Another fluoro compound that may form part of the composition of the fluoro phase of the second composition includes fluoro polyethers of formula (III) below:

wherein:
- $R_4$ to $R_7$ represent, independently of each other, a monovalent radical chosen from —F, —$(CF_2)$n-$CF_3$ and —O—$(CF_2)$n-$CF_3$;
- $R_8$ represents a monovalent radical selected from —F and —$(CF_2)$n-$CF_3$, wherein n ranges from 0 to 4 inclusive,
- p ranges from 0 to 600, q ranges from 0 to 860, r ranges from 0 to 1,500, and p, q and r are integers selected such that the weight-average molecular weight of the compound ranges from 500 to 100,000 and preferably from 500 to 10,000.

Such compounds are especially described in document EP-A-0 196 904.

Suitable commercial products that may be used include a fluoro compound of the likes of the Fomblins manufactured by Montefluos, and the Demnum S products manufactured by Daikin Industries.

Suitable fluoro compounds that may be used in the present invention include fluoroalkanes, such as $C_2$–$C_{50}$ and especially $C_5$–$C_{30}$-perfluoroalkanes and fluoroalkanes, such as perfluorodecalin, perfluoroadamantane and bromoperfluorooctyl.

The physiologically acceptable medium of the second composition may also contain a volatile silicone-based and/or fluoro-based liquid phase whose rate of evaporation is different than the rate of evaporation of the volatile phase of the first composition, and in particular the rate of evaporation of the volatile phase of the second composition is less than the rate of evaporation of the volatile phase of the first composition.

The silicone-based and/or fluoro-based liquid phase of the second composition represents from 1% to 100%, preferably from 5% to 95%, better still from 20% to 80% and even better still from 40% to 80% of the total weight of the second composition.

Coloring Agent

The first and/or second composition(s) of the invention may contain a coloring agent which may be selected from liposoluble or water-soluble dyes, pigments and nacres, and mixtures thereof.

Preferably, the first composition contains one or more coloring agents, advantageously in the form of a dispersion.

The term "pigments" should be understood as meaning white or colored, mineral or organic particles that are insoluble in the organic or aqueous liquid phase of the first or second composition, intended to color and/or opacify the composition. The term "nacres" should be understood to mean iridescent particles, especially produced by certain mollusks in their shell or alternatively synthesized that are insoluble in the medium of the first or second composition.

The term "dyes" should be understood as meaning generally organic compounds that are soluble in the fatty substances, for instance the oils, or in an aqueous-alcoholic phase.

The liposoluble dyes are, for example, Sudan red, D&C Red No. 17, D&C Green No. 6, β-carotene, soybean oil, Sudan brown, D&C Yellow No. 11, D&C Violet No. 2, D&C Orange No. 5, quinoline yellow, annatto and bromoacids. Suitable water-soluble dyes include, for example, beetroot juice, methylene blue and caramel.

The pigments may be white or colored, mineral and/or organic, and interference or non-interference pigments. Suitable mineral pigments include titanium dioxide, optionally surface-treated, zirconium oxide or cerium oxide, and also zinc oxide, iron oxide (black, yellow, brown or red) or chromium oxide, manganese violet, ultramarine blue, chromium hydrate and ferric blue. Suitable organic pigments include carbon black, pigments of the type such as barium, strontium, calcium or aluminum organic lakes, including those subject to certification by the Food and Drug Administration (FDA) (example: D&C or FD&C) and those exempt from FDA certification, for instance lakes based on cochineal carmine.

The nacres or nacreous pigments may be selected from white nacreous pigments such as mica coated with titanium or with bismuth oxychloride, colored nacreous pigments such as titanium mica with iron oxides, titanium mica with, especially, ferric blue or chromium oxide, titanium mica with an organic pigment of the above-mentioned type and also nacreous pigments based on bismuth oxychloride. Pigments with goniochromatic properties, especially with liquid crystal or multilayer properties, may thus be used.

In general, the coloring agents represent from 0.001% to 60%, better still from 0.01% to 50% and even better still from 0.1% to 40% of the total weight of the first or the second composition, respectively.

The coloring agent or the filler may also be present in the form of a "particulate paste".

Particulate Paste

For the purposes of the invention, the expression "particulate paste" means a concentrated dispersion of coated or uncoated particles in a continuous medium, stabilized with a dispersant or optionally without a dispersant. These particles may be selected from pigments, nacres, solid fillers and mixtures thereof. These particles may be of any shape, especially of spherical or elongated shape, for instance fibers. They are insoluble in the medium.

The dispersant serves to prevent the dispersed particles from aggregating or flocculating. The dispersant concentration generally used to stabilize a dispersion ranges from 0.3 to 5 mg/m$^2$, preferably from 0.5 to 4 mg/m$^2$ of the surface area of particles. This dispersant may be a surfactant, an oligomer, a polymer or mixtures thereof, bearing one or more functional group having a strong affinity for the surface of the particles to be dispersed. In particular, they may attach physically or chemically to the surface of pigments. These dispersants also contain at least one functional group that is compatible with or soluble in the continuous medium. In particular, poly(12-hydroxystearic acid) such as that sold under the name Arlacel P100 manufactured by Uniqema, esters of (12-hydroxystearic acid) such as the stearate of poly(12-hydroxystearic acid) with a molecular weight of about 750 g/mol sold under the name Solsperse 21 000 manufactured by Avecia, esters of poly(12-hydroxystearic acid) with polyols such as glycerol, diglycerin such as the polyglyceryl-2 dipolyhydroxy-stearate (CTFA name) sold under the name Dehymuls PGPH manufactured by Henkel.

Suitable other dispersants which may be used in the composition of the invention, include quaternary ammonium derivatives of polycondensed fatty acids, for instance Solsperse 17 000 sold by Avecia, and mixtures of polydimethylsiloxane/oxypropylene, such as those sold by Dow Corning under the names DC2-5185 and DC2-3225 C.

Poly(12-hydroxystearic acid) and the poly(12-hydroxystearic acid) esters are preferably intended for a hydrocarbon-based or fluorinated medium, whereas the mixtures of oxyethylenated/oxypropylenated dimethylsiloxane are preferably intended for a silicone medium.

The dispersion is a suspension of particles that are generally micron-sized (<10 µm) in a continuous medium. The volume fraction of particles in a concentrated dispersion ranges from 20% to 40%, preferably greater than 30%, which corresponds to a weight content that may range up to 70% depending on the density of the particles.

The particles dispersed in the medium may consist of mineral or organic particles or mixtures thereof, such as those described below.

The continuous medium of the paste may be of any nature and may contain any solvent or liquid fatty substance and mixtures thereof. Advantageously, the liquid medium of the particulate paste is one of the liquid fatty substances or oils that is desirably used in the first or second composition, thus forming part of the liquid organic phase of the first or second composition.

Advantageously, the "particulate paste" is a "pigmentary paste" containing a dispersion of coated or uncoated colored particles. These colored particles are pigments, nacres or a mixture of pigments and/or nacres such as those described above.

Preferably, the coloring agent for the first composition is in the form of a dispersion or particulate paste as described above.

Advantageously, the dispersion represents from 0.5% to 60% by weight of each first and/or second composition, better still from 2% to 40% and even better still from 2% to 30%.

Additives

The first and/or second compositions in the make-up product of the invention may also contain one or more cosmetic, dermatological, hygiene or pharmaceutical active agents. Suitable cosmetic, dermatological, hygiene or pharmaceutical active agents that may be used in the compositions of the invention include moisturizers such as polyols, for instance glycerol), vitamins (C, A, E, F, B or PP), essential fatty acids, essential oils, ceramides, sphingolipids, liposoluble sunscreens or sunscreens in the form of nanoparticles, and specific skin-treatment active agents (protective agents, antibacterial agents, antiwrinkle agents, and the like).

These active agents are used in an amount that is usual for a person skilled in the art and especially at concentrations ranging from 0% to 20% and especially from 0.001% to 15% relative to the total weight of the first or second composition.

Each composition of the process of the invention may furthermore comprise, depending on the intended type of application, the constituents conventionally used in the fields under consideration, which are present in an amount that is suitable for the desired presentation form.

In general, the physiologically acceptable media for each of the first and second compositions of the process of the invention may comprise, in addition to the liquid phase and the polymer dispersion for the first composition and the silicone-based and/or fluoro-based liquid phase for the second composition, additional fatty substances that may be selected from waxes, oils, gums and/or pasty fatty substances, that are hydrocarbon-based, silicone-based and/or fluoro-based, of plant, animal, mineral or synthetic origin, and mixtures thereof.

Preferably, the physiologically acceptable medium for the first composition contains a gum, preferably a silicone gum with a viscosity at room temperature ranging from 50,000 to $10^7$ cSt and preferably from 100,000 to $10^6$ cSt.

Preferably, the physiologically acceptable medium for the first and/or the second composition contains a pasty fatty substance and/or a wax selected from the waxes mentioned above.

Each composition of the process of the invention may also contain any other additive usually used in such compositions, for instance oil thickeners or aqueous-phase thickeners (acrylic gelling agent), antioxidants, fragrances, preserving agents (pentylene glycol), surfactants or liposoluble polymers (for example polyvinylpyrrolidone/eicosene copolymer), and mixtures thereof.

When the physiologically acceptable medium for the first and/or the second composition contains a liquid organic phase, this medium may especially contain water dispersed or emulsified in the liquid organic phase.

In one specific embodiment of the invention, the compositions of the process of the invention can be prepared in the usual manner by a person skilled in the art. They can be in the form of a cast product and, for example, in the form of a stick or tube, in the form of a soft paste in a heating bag or in the form of a dish which can be used by direct contact or with a sponge. In particular, they constitute, alone or combined, a cast foundation, a cast in particular colored, face powder or eye shadow, a lipstick, a lip gloss or a concealer product. They can also be in the form of a soft paste or alternatively in the form of a gel or a more or less fluid cream. In this case, they can constitute foundations or lipsticks that are fluid or pasty, lip glosses, antisun products or skin-coloring products, eyeliner or body make-products, or alternatively they may have care properties and may then be in the form of a lipcare balm or base.

Each composition used in the process of the invention may be in any presentation form normally used for topical application and especially in the form of an oily or aqueous solution, an oily or aqueous gel, an oil-in-water or water-in-oil emulsion, a multiple emulsion or a dispersion of oil in water by means of vesicles, the vesicles being located at the oil/water interface, or a powder. Each composition may be fluid or solid.

Advantageously, the first or second composition, or both of them, have a continuous fatty phase and are preferably in anhydrous form and may contain less than 5% water, and better still less than 1% water, relative to the total weight of the first or second composition. In particular, the whole two-coat makeup product is in anhydrous form.

Each first and second composition may have the appearance of a lotion, a cream, an ointment, a soft paste, a salve, a cast or molded solid, which is especially in stick or dish form, or alternatively a compacted solid.

Preferably, each composition is in the form of a more or less rigid stick.

Each composition may be packaged separately in the same packaging article, for example, in a two-compartment pen, the base composition being delivered from one end of the pen and the top composition being delivered from the other end of the pen, each end being closed, especially in a leaktight manner, by a cap.

Preferably, the composition that is applied as a first coat is in solid form, thus allowing a more practical application, better stability over time and at elevated temperature for the composition, and allows the make-up to be applied in a precise line, which is highly desirable in the case of a lipstick or an eyeliner.

The process of the invention may advantageously be used for making-up the skin and/or the lips and/or integuments depending on the nature of the ingredients used. In particular, each composition of the invention may be in the form of a tube of lipstick or lipstick paste, a solid foundation, a concealer product or products for the contours of the eyes, an eyeliner, a mascara, an eyeshadow, a body makeup product or a skin coloring product.

A particularly desirable form of the compositions is as a lipstick.

Advantageously, the topcoat has care properties.

The compositions of the invention may be prepared by heating the various constituents to the temperature of the highest-melting waxes, followed by casting the molten mixture in a mold (dish or glove digit). They may also be obtained by extrusion, as described in patent application EP-A-0 667 146.

Having generally described this invention, a further understanding can be obtained by reference to certain specific examples which are provided herein for purposes of illustration only and are not intended to be limiting unless otherwise specified. The amounts are given as percentages by weight.

EXAMPLES

Example 1

Polymer Dispersion

A dispersion of non-crosslinked copolymer of methyl acrylate and of acrylic acid in a 95/5 ratio in isododecane is prepared, according to the method of Example 1 described in EP-A-749 746, except replacing the heptane with isododecane. A dispersion of poly(methyl acrylate/acrylic acid) particles surface-stabilized in isododecane with a polystyrene/copoly(ethylene-propylene) block diblock copolymer sold under the name Kraton G1701 (Shell), having a solids content of 24.6% by weight and a mean particle size of 180 nm (polydispersity: 0.05%) and a Tg of 20° C., is thus obtained. This copolymer is capable of forming a film.

Example 2

Pigmentary Paste

The pigmentary paste used is a mixture of 3 pigmentary pastes each containing a different pigment:

| Paste No. 1: | |
|---|---|
| DCRed No. 7 | 30% |
| Poly(12-hydroxystearic acid) stearate (Solsperse 21000) | 2% |
| Hydrogenated polyisobutene (Parleam) | 68% |
| Paste No. 2: | |
| Yellow No. 6 Al lake | 50% |
| Poly(12-hydroxystearic acid) stearate (Solsperse 21000) | 2% |
| Hydrogenated polyisobutene (Parleam) | 48% |
| Paste No. 3: | |
| Titanium dioxide | 70% |
| Poly(12-hydroxystearic acid) stearate (Solsperse 21000) | 1% |
| Hydrogenated polyisobutene (Parleam) | 29% |

A pigmentary paste containing a mixture of 10% of paste No. 1, 2% of paste No. 2 and 2.14% of paste No. 3 is produced.

Example 3

Lip Make-Up Product

| First composition | |
|---|---|
| Phase A | |
| polymer particle dispersion of Example 1 | 71% |
| ethylene/octene copolymer (76/24) sold under the name Engage 8400 manufactured by Dupont de Nemours | 3.50% |
| Phase B | |
| pigmentary paste of Example 2 | 14.14% |
| Phase C | |
| polytetrafluoroethylene | 10% |
| Phase D | |
| cyclopentasiloxane | 1.36% |

Procedure

Phase A is prepared by dissolving the gelling agent (ethylene/octene copolymer) at 110° C. in the polymer particle dispersion over about one hour using a Raynerie mixer. After homogenization, the temperature is allowed to return to about 30° C. and phases B, C and D are then successively added with stirring using a Raynerie mixer. The first composition is then packaged in a heating bag at room temperature. It is in the form of a soft paste.

| Second composition | |
|---|---|
| phenyltrimethicone (with a viscosity equal to 20 cSt) sold under the name DC 556 manufactured by Dow Corning | 46% |
| phenyltrimethicone (with a viscosity equal to 1000 cSt) sold under the name Belsil PDM 1000 manufactured by Wacker | 46% |
| polyethylene wax (Mw* = 500) | 8% |

*Mw represents weight-average molecular weight.

Procedure

The constituents of the second composition are weighed out together and heated at 100° C. until the wax has completely melted. After homogenization, the composition can be cast in a suitable mold to obtain a stick in the form of a "pen". A first coat of the first composition is then applied to the lips using a felt, and then left to dry for 3 minutes. A second coat of the second composition is then applied over this first coat.

A glossy two-coat lip makeup is obtained, which is comfortable, does not have a dehydrating effect, has good staying power, does not migrate and does not transfer onto a cup or fabric after drying for about 2 minutes. These properties were checked and confirmed by qualified individuals.

Example 4

Lip Makeup Product

| First composition | |
|---|---|
| Phase A | |
| polymer particle dispersion of Example 1 | 71% |
| PVP/eicosene copolymer | 3.5% |
| Phase B | |
| pigmentary paste of Example 2 | 14.14% |
| Phase C | |
| polytetrafluoroethylene | 10% |
| Phase D | |
| cyclopentasiloxane | 1.36% |

The same manufacturing procedure and the same procedure for application to the lips as those of the first composition of Example 3 are used.

The second composition of Example 3 is applied as a topcoat according to the same procedure.

The make-up product obtained has the same properties as those of the product of Example 3.

Example 5

Lip Make-Up Product

| First composition | |
|---|---|
| Phase A | |
| polymer particle dispersion of Example 1 | 75.5% |
| ethylene/octene copolymer (76/24) sold under the name Engage 8400 manufactured by Dupont de Nemours | 3.50% |
| Phase B | |
| pigmentary paste of Example 2 | 14.14% |
| Phase C | |
| polytetrafluoroethylene | 5% |
| Phase D | |
| cyclopentasiloxane | 1.36% |

The same manufacturing procedure as that for the first composition of Example 3 is used.

| Second composition | |
|---|---|
| phenyltrimethicone (with a viscosity equal to 20 cSt) sold under the name DC 556 manufactured by Dow Corning | 42% |
| Phenyltrimethicone (with a viscosity equal to 1000 cSt) sold under the name Belsil PDM 1000 manufactured by Wacker | 42% |
| fluorosilicone sold under the name X 22819 manufactured by Shin-Etsu | 8% |
| polyethylene wax (Mw* = 500) | 8% |

Procedure

The constituents of the second composition are weighed together and heated to 100° C. until the wax has completely melted.

After homogenization, the composition can be cast into a suitable mold to obtain a stick in the form of a "pencil".

A first coat of the first composition is applied to the lips using a felt and is left to dry for about 3 minutes. A second coat of the second composition is then applied over this first coat.

A glossy two-coat lip make-up is obtained, which is comfortable (does not make the skin taut), has good staying power, does not migrate, does not transfer and is easy to remove. These properties were checked and confirmed by qualified individuals.

Example 6

Lip Make-Up Product

| First composition | |
|---|---|
| Phase A | |
| polymer particle dispersion of Example 1 | 71% |
| polyethylene wax sold under the name AC 617 manufactured by Honeywell | 3.5% |
| Phase B | |
| pigmentary paste of Example 2 | 14.14% |
| Phase C | |
| polytetrafluoroethylene | 10% |
| Phase D | |
| cyclopentasiloxane | 1.36% |

The same manufacturing and application procedure as that for the first composition of Example 3 is used.

The second composition of Example 3 is applied as a top coat. The use of the product is the same as that of Example, as are its cosmetic make-up properties.

Example 7

Lip Make-Up Product

| First composition | |
|---|---|
| Phase A | |
| polymer particle dispersion of Example 1 | 75% |
| hectorite modified with distearyldimethylammonium chloride, sold under the name Bentone 38 VCG manufactured by Elementis | 3.38% |

-continued

| First composition | |
|---|---|
| propylene carbonate | 1.12% |
| Phase B | |
| pigmentary paste of Example 2 | 14.14% |
| Phase C | |
| polytetrafluoroethylene | 5% |
| Phase D | |
| cyclopentasiloxane | 1.36% |

Procedure

Phase A is obtained by slowly adding the modified hectorite with stirring using a Raynerie mixer at room temperature (25° C.).

The propylene carbonate is then added with continued stirring.

After homogenization, phases B, C and D are successively added at room temperature with continued stirring using a Raynerie mixer.

The composition is then packaged in a heating bag at room temperature. It is in the form of a soft paste and is applied with a felt.

This first composition is applied to the lips and is then left to dry for 3 minutes.

The second composition of Example 3 is applied as a topcoat, according to the same procedure as that in this example. The two-coat makeup obtained has the same properties in terms of comfort, staying power, absence of transfer and absence of migration as those of the product of Example 3.

Example 8

Lip Make-Up Product

| First composition | |
|---|---|
| Phase A | |
| polymer particle dispersion of Example 1 | 69.16% |
| Phase B | |
| pigmentary paste of Example 2 | 14.14% |
| Phase C | |
| polyethylene wax (Mw = 500) | 12% |
| ozokerite | 3.20% |
| linear fatty alcohol sold under the name Performacol 550 manufactured by New Phase Technologies | 1.50% |

Procedure

The constituents of the first composition are all weighed and mixed together at 100–105° C. using a Raynerie mixer. After homogenization, the composition is cast at 100° C. into a mold and packaged in the form of a "pencil". This first composition is then applied to the lips, after which it is left to dry for 3 minutes.

The second composition of Example 3 is applied as a topcoat according to the same procedure. The cosmetic make-up properties of the product are in accordance with those of the product of Example 3.

Example 9

Eyeshadow

| First composition | |
|---|---|
| polymer particle dispersion of Example 1 | 75.6% |
| parleam oil | 6.4% |
| nylon powder | 8% |
| ultramarine blue | 10% |

The various ingredients are mixed together at room temperature using a Raynerie mixer.

A first coat of this first composition is applied to each eyelid. The composition is left to dry for about 3 minutes and the second composition of Example 3 is then applied as a topcoat onto the eyelids.

A glossy two-coat make-up is obtained, which is comfortable, has good staying power, does not migrate into the folds and fine lines of the eyelids and does not transfer onto fabric placed in contact with the eyes.

Example 10

Lip Make-Up Product

| First composition | | |
|---|---|---|
| aqueous dispersion of acrylic/styrene polymer (Neocryl A-1070 from Zeneca) containing 45% active material | | 8.5% |
| red iron oxide | | 1.5% |
| DC Red 30 | | 0.4% |
| mica/titanium dioxide | | 3.1% |
| acrylic gelling agent | | 4.9% |
| pentylene glycol | | 3% |
| squalane | | 10% |
| water | qs | 100% |

The various constituents of the first composition are mixed together at room temperature and are then introduced into a heating bag.

Using a felt that is impregnated with this first composition, a basecoat of a two-coat lipstick is applied to the lips. This coat is left to dry for about 5 minutes and the second composition of Example 3 is then applied. A glossy two-coat make-up is obtained, which does not migrate, is transfer-resistant and is easy to remove.

The make-up products of the above examples are easy to remove with standard waterproof make-up remover such as Bifacil manufactured by Lancôme.

The disclosures of French applications Serial Number 0104940 filed Oct. 4, 2001 and Serial Number 0201444 filed Jun. 2, 2002, and provisional application Serial No. 60/293980, filed May 30, 2001, are hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A process for applying cosmetic to the skin and/or the lips and/or integuments of a human being, which comprises:
applying to the skin, the lips and/or integuments a first coat of a first composition comprising, in a first physiologically acceptable medium, dispersed polymer particles surface-stabilized with a stabilizer in a liquid phase;

permitting the first coat to dry; and then
applying over all or a part of the first coat, a second coat of a second composition comprising, in a second physiologically acceptable medium, a silicone-based and/or fluoro-based liquid phase.

2. The process as claimed in claim 1, wherein the polymer particles have a mean size ranging from 5 to 800 nm.

3. The process as claimed in claim 1, wherein the polymer particles are insoluble in water-soluble alcohols.

4. The process as claimed in claim 1, wherein the polymer particles are selected from the group consisting of polyurethanes, polyurethane-acrylics, polyureas, polyurea-polyurethanes, polyester-polyurethanes, polyether-polyurethanes, polyesters, polyesteramides, alkyl fatty-chain polyesters, acrylic polymers, acrylic copolymers, vinyl copolymers, vinyl polymers, acrylic-silicone copolymers, polyacrylamides, silicone polymers, fluoro polymers, and mixtures thereof.

5. The process as claimed in claim 1, wherein the polymer is capable of forming a film.

6. The process as claimed in claim 1, wherein the polymer represents, as solids, from 2% to 40% relative to the total weight of the first composition.

7. The process as claimed in claim 6, wherein the polymer represents, as solids, from 5% to 30%.

8. The process as claimed in claim 7, wherein the polymer represents, as solids, from 8% to 20%.

9. The process as claimed in claim 1, wherein the stabilizer is selected from block polymers, graft polymers, random polymers, and mixtures thereof.

10. The process as claimed in claim 1, wherein the stabilizer is selected from the group consisting of silicone polymers having a hydrocarbon-based chain graft, hydrocarbon-based polymers having a silicone chain graft, graft copolymers baying an insoluble polyacrylic backbone with soluble grafts of poly(12-hydroxystearic acid), grafted-block copolymers comprising at least one polyorganosiloxane block and at least one black of a free-radical polymer, block copolymers comprising at least one polyorganosiloxane block and at least one block of a free-radical polymer, grafted-block copolymers comprising at least one polyorganosiloxane block and at least one block of a polyether, block copolymers comprising at least one polyorganosiloxane block and at least one block of a polyether, copolymers of $C_1$–$C_4$-alkyl acrylates, copolymers of $C_1$–$C_4$-alkyl methacrylates, copolymers of $C_8$–$C_{30}$ alkyl acrylates, copolymers of $C_8$–$C_{30}$ alkyl methacrylates, grafted-block copolymers comprising at least one block resulting from the polymerization of ethylenic monomers optionally comprising conjugated bonds and at least one block of a vinyl polymer, block copolymers comprising at least one block resulting from the polymerization of ethylenic monomers optionally comprising conjugated bonds and at least one block of a vinyl polymer, grafted-block comprising at least one block resulting from the polymerization of ethylenic monomers optionally comprising conjugated bonds and at least one block of an acrylic polymer, block copolymers comprising at least one block resulting from the polymerization of ethylenic monomers optionally comprising conjugated bonds and at least one block of an acrylic polymer, grafted-block copolymers comprising at least one block resulting from the polymerization of diene and at least one block of a polyether, block copolymers comprising at least one block resulting from the polymerization of diene and at least one block of a polyether, and mixtures thereof.

11. The process as claimed in claim 1, wherein the stabilizer is a grafted-block or block polymer comprising at least one block resulting from the polymerization of diene and at least one block of a vinyl polymer.

12. The process as claimed in claim 1, wherein the stabilizer is a diblock polymer.

13. The process as claimed in claim 1, wherein the liquid phase of the first composition is a liquid organic phase.

14. The process as claimed in claim 1, wherein the liquid organic phase comprises at least one organic oil that is volatile at room temperature and atmospheric pressure.

15. The process as claimed in claim 1, wherein the volatile organic oil represents from 20% to 90% of the total weight of the first composition.

16. The process as claimed in claim 15, wherein the volatile organic oil represents from 30% to 80% of the total weight of the first composition.

17. The process as claimed in claim 16, wherein the volatile organic oil represents from 40% to 70% of the total weight of the first composition.

18. The process as claimed in claim 1, wherein the first composition further comprises a rheological agent which structures and/or gels its physiologically acceptable medium, said agent being selected from the group consisting of lipophilic gelling agents, waxes, fillers, and mixtures thereof.

19. The process as claimed in claim 18, wherein the rheological agent represents from 0.1% to 50% of the total weight of the first composition.

20. The process as claimed in claim 19, wherein the rheological agent represents from 1% to 25% of the total weight of the first composition.

21. The process as claimed in claim 18, wherein the rheological agent comprises a lipophilic gelling agent selected from the group consisting of ethylene homopolymer with a weight average molecular weight ranging from 300 to 500,000, ethylene copolymers with a weight average molecular weight ranging from 300 to 500,000, and mixtures thereof.

22. The process as claimed in claim 21, wherein the rheological agent comprises a lipophilic gelling agent selected from the group consisting of ethylene homopolymers with a weight average molecular weight ranging from 500 to 100,000, ethylene copolymers with a weight average molecular weight ranging from 500 to 100,000, and mixtures thereof.

23. The process as claimed in claim 18, wherein the rheological agent is an ethylene/octene copolymer.

24. The process as claimed in claim 18, wherein the rheological agent represents from 0.5% to 20% of the total weight of the first composition.

25. The process as claimed in claim 24, wherein the rheological agent represents from 1% to 10% of the total weight of the first composition.

26. The process as claimed in claim 18, wherein the rheological agent comprises a wax.

27. The process as claimed in claim 26, wherein the wax is present in an amount of from 0.1% to 50% by weight in the first composition.

28. The process as claimed in claim 27, wherein the wax is present in an amount of from 3% to 25% by weight in the first composition.

29. The process as claimed in claim 18, wherein the rheological agent comprises a filler.

30. The process as claimed in claim 29, wherein the filler has a particle size of less than 50 $\mu$m.

31. The process as claimed in claim 29, wherein the filler is selected from the group consisting of talc, mica, silica, kaolin, polyamide powders, poly-β-alanine powders, polyethylene powders, powders of tetrafluoroethylene polymers, lauroyllysine, starch, boron nitride, hollow polymer microspheres, acrylic polymer particles, silicone resin microbeads, precipitated calcium carbonate, dicalcium phosphate, magnesium carbonate, magnesium hydrocarbonate, hydroxyapatite, hollow silica microspheres, glass, ceramic microcapsules, metal soaps derived from organic $C_8$–$C_{22}$ carboxylic acids, and mixtures thereof.

32. The process as claimed in claim 29, wherein the filler represents from 0.1% to 35% of the total weight of the first composition.

33. The process as claimed in claim 32, wherein the filler represents from 0.5% to 25% of the total weight of the first composition.

34. The process as claimed in claim 33, wherein the filler represents from 1% to 15% of the total weight of the first composition.

35. The process as claimed in claim 1, wherein the silicone-based and/or fluoro-based liquid phase of the second composition comprises a liquid phase that is nonvolatile at room temperature and atmospheric pressure.

36. The process as claimed in claim 35, wherein the nonvolatile liquid phase contains at least one phenylsilicone oil.

37. The process as claimed in claim 36, wherein the phenylsilicone oil has a viscosity, measured at 25° C., ranging from 5 to 100 000 cSt.

38. The process as claimed in claim 37, wherein the phenylsilicone oil has a viscosity, measured at 25° C., ranging from 5 to 10 000 cSt.

39. The process as claimed in claim 36, wherein the silicone oil is selected from the group consisting of phenylsilicone oils of formula (A) below:

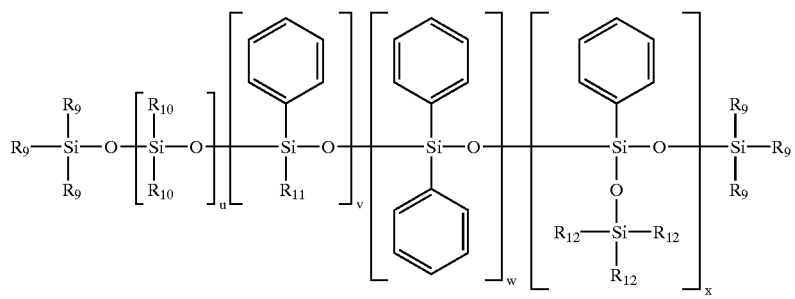

wherein
$R_9$ and $R_{12}$ are each independently a $C_1$–$C_{30}$-alkyl radical, an aryl radical or an aralkyl radical,
$R_{10}$ and $R_{11}$ are each independently a $C_1$–$C_{30}$-alkyl radical or an aralkyl radical,
u, v, w and x are each independently integers ranging from 0 to 900, with the proviso that the sum v+w+x is other than 0 and that the sum u+v+w+x ranges from 1 to 900.

40. The process as claimed in claim 37, wherein the nonvolatile liquid phase comprises a low-viscosity phenylsilicone oil and a high-viscosity phenylsilicone oil.

41. The process as claimed in claim 40, wherein the low-viscosity phenylsilicone oil has a viscosity at 25° C. ranging from 5 to 499 cSt and the high-viscosity phenylsilicone oil has a viscosity at 25° C. ranging from 500 to 10,000 cSt.

42. The process as claimed in claim 41, wherein the low-viscosity phenylsilicone oil has a viscosity ranging from 5 to 300 cSt at 25° C. and the high-viscosity phenylsilicone oil has a viscosity ranging from 600 to 5,000 cSt at 25° C.

43. The process as claimed in claim 40, wherein the low-viscosity phenylsilicone oil satisfies formula (I) below:

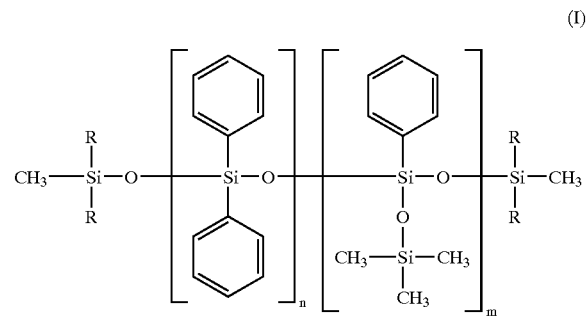

wherein
R is a $C_1$–$C_{30}$-alkyl radical, an aryl radical or an aralkyl radical,
n is an integer ranging from 0 to 100,
m is an integer ranging from 0 to 100, with the proviso that the sum m+n ranges from 1 to 100.

44. The process as claimed in claim 41, wherein the weight ratio of the low-viscosity phenylsilicone oil to the high-viscosity phenylsilicone oil ranges from 70/30 to 30/70.

45. The process as claimed in claim 44, wherein the weight ratio of the low-viscosity phenylsilicone oil to the high-viscosity phenylsilicone oil ranges from 60/40 to 40/60.

46. The process as claimed in claim 45, wherein the nonvolatile liquid phase comprises at least one fluoro compound selected from the group consisting of fluorosilicone compounds, fluoro polyethers and fluoroalkanes.

47. The process as claimed in claim 46, wherein the fluorosilicone compounds are selected from the group consisting of compounds of formula (II):

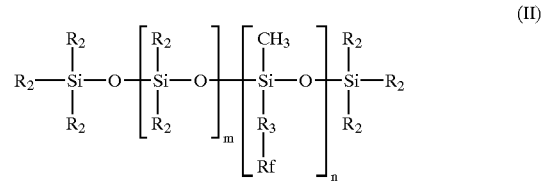

wherein:
$R_3$ represents a $C_1$–$C_6$ linear or branched divalent alkyl group,
Rf represents a $C_1$–$C_9$ fluoroalkyl radical, $R_2$ represent, independently of each other, a $C_1$–$C_{20}$ alkyl radical, a hydroxyl radical or a phenyl radical, m is a value from 0 to 150 and n is a value from 1 to 300.

48. The process as claimed in claim 46, wherein the fluoro polyethers are selected from the group consisting of compounds of formula (III):

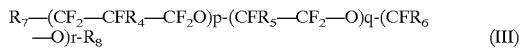
$$R_7—(CF_2—CFR_4—CF_2O)p-(CFR_5—CF_2—O)q-(CFR_6—O)r-R_8 \quad (III)$$

wherein:

$R_4$ to $R_7$ represent, independently of each other, a monovalent radical selected from the group consisting of —F, —$(CF_2)n$-$CF_3$ and —O—$(CF_2)n$-$CF_3$;

$R_8$ represents a monovalent radical selected from the group consisting of —F and —$(CF_2)n$-$CF_3$;

with n ranging from 0 to 4; p ranging from 0 to 600, q ranging from 0 to 860, r ranging from 0 to 1,500, and p, q and r being integers selected such that the weight-average molecular weight of the compound ranges from 500 to 100,000.

49. The process as claimed in claim 46, wherein the fluoroalkanes are selected from the group consisting of $C_2$–$C_{50}$-perfluoroalkanes and fluoroalkanes.

50. The process as claimed in claim 1, wherein the silicone-based and/or fluoro-based liquid phase represents from 1% to 100% of the total weight of the second composition.

51. The process as claimed in claim 50, wherein the silicone-based and/or fluoro-based liquid phase represents from 5% to 95% of the total weight of the second composition.

52. The process as claimed in claim 1, wherein the physiological acceptable medium of the first and/or second composition contains a coloring agent.

53. The process as claimed in claim 52, wherein the coloring agent is selected from the group consisting of liposoluble dyes, water-soluble dyes, pigments, nacres, and mixtures thereof.

54. The process as claimed in claim 1, wherein the first composition contains a coloring agent in the form of a dispersion.

55. The process as claimed in claim 52, wherein the coloring agent is present in an amount ranging from 0.001% to 60% of the total weight of the first or the second composition, respectively.

56. The process as claimed in claim 55, wherein the coloring agent is present in an amount ranging from 0.01% to 50% of the total weight of the first or the second composition, respectively.

57. The process as claimed in claim 1, wherein the physiologically acceptable medium for the first and/or second composition comprises one or more cosmetic or dermatological active agents.

58. The process as claimed in claim 57, wherein the physiologically acceptable medium for the first and/or second composition comprises a fatty substance selected from the group consisting of waxes, oils, gums and pasty fatty substances.

59. The process as claimed in claim 1, wherein the physiologically acceptable medium for the first composition comprises a gum.

60. The process as claimed in claim 59, wherein the gum is a silicone gum.

61. The process as claimed in claim 1, wherein the physiologically acceptable medium for the second composition comprises a pasty fatty substance and/or a wax.

62. The process as claimed in claim 1, wherein the physiologically acceptable medium for the first and/or second composition also comprises at least one additive selected from the group consisting of oil thickeners, aqueous-phase thickeners, antioxidants, fragrances, preserving agents, surfactants, liposoluble polymers, and mixtures thereof.

63. The process as claimed in claim 1, wherein each composition is in the form of an oily solution, an aqueous solution, an oily gel, an aqueous gel, an oil-in-water emulsion, a water-in-oil emulsion, a multiple emulsion, a dispersion of oil in water by means of vesicles, or a powder.

64. The process as claimed in claim 1, wherein each composition is in the form of a foundation, a face powder, an eyeshadow, a lipstick, a lipcare base, a balm, an eyeliner, a concealer product or a body makeup product.

65. The process as claimed in claim 1, wherein the first or second composition, or both of them, is(are) in anhydrous form.

66. The cosmetic make-up process as claimed in claim 1, which improves properties in terms of comfort and/or gloss and/or transfer and/or migration and/or staying power of makeup on the skin and/or the lips and/or integuments of human beings.

67. The process of claim 1, wherein the cosmetic is applied to the lips.

68. The process of claim 1, wherein the second composition comprises a silicone-based liquid phase.

69. The process of claim 3, wherein the cosmetic is applied to the lips.

70. The process of claim 3, wherein the second composition comprises a silicone-based liquid phase.

71. The process of claim 3, wherein the polymer particles have a mean size ranging from 5 to 800 nm.

72. The process of claim 3, wherein the polymer is capable of forming a film.

73. The process as claimed in claim 3, wherein the polymer represents, as solids, from 2% to 40% relative to the total weight of the first composition.

74. The process as claimed in claim 73, wherein the polymer represents, as solids, from 5% to 30%.

75. The process as claimed in claim 73, wherein the polymer represents, as solids, from 8% to 20%.

76. The process as claimed in claim 3, wherein the stabilizer is selected from block polymers, graft polymers, random polymers, and mixtures thereof.

77. The process as claimed in claim 3, wherein the stabilizer is a grafted-block or block polymer comprising at least one block resulting from the polymerization of diene and at least one block of a vinyl polymer.

78. The process as claimed in claim 3, wherein the stabilizer is a diblock polymer.

79. The process as claimed in claim 3, wherein the liquid phase of the first composition is a liquid organic phase.

80. The process as claimed in claim 79, wherein the liquid organic phase comprises at least one organic oil that is volatile at room temperature and atmospheric pressure.

81. The process as claimed in claim 3, wherein the volatile organic oil represents from 20% to 90% of the total weight of the first composition.

82. The process as claimed in claim 81, wherein the volatile organic oil represents from 30% to 80% of the total weight of the first composition.

83. The process as claimed in claim 82, wherein the volatile organic oil represents from 40% to 70% of the total weight of the first composition.

84. The process as claimed in claim 3, wherein the first composition further comprises a rheological agent which thickens and/or gels its physiologically acceptable medium, said agent being selected from the group consisting of lipophilic gelling agents, waxes, fillers, and mixtures thereof.

85. The process as claimed in claim 84, wherein the rheological agent represents from 0.1% to 50% of the total weight of the first composition.

86. The process as claimed in claim 84, wherein the rheological agent represents from 1% to 25% of the total weight of the first composition.

87. The process as claimed in claim 84, wherein the rheological agent comprises a lipophilic gelling agent selected from the group consisting of ethylene homopolymer with a weight average molecular weight ranging from 300 to 500,000, ethylene copolymers with a weight average molecular weight ranging from 300 to 500,000, and mixtures thereof.

88. The process as claimed in claim 87, wherein the rheological agent comprises a lipophilic gelling agent selected from the group consisting of ethylene homopolymers with a weight average molecular weight ranging front 500 to 100,000, ethylene copolymers with a weight average molecular weight ranging from 500 to 100,000, and mixtures thereof.

89. The process as claimed in claim 84, wherein the rheological agent is an ethylene/octene copolymer.

90. The process as claimed in claim 84, wherein the rheological agent represents from 0.5% to 20% of the total weight of the first composition.

91. The process as claimed in claim 90, wherein the rheological agent represents from 1% to 10% of the total weight of the first composition.

92. The process as claimed in claim 84, wherein the rheological agent comprises a wax.

93. The process as claimed in claim 92, wherein the wax is present in an amount of from 0.1% to 50% by weight in the first composition.

94. The process as claimed in claim 93, wherein the wax is present in an amount of from 3% to 25% by weight in the first composition.

95. The process as claimed in claim 84, wherein the rheological agent comprises a filler.

96. The process as claimed in claim 95, wherein the filler has a particle size of less than 50 μm.

97. The process as claimed in claim 95, wherein the filler is selected from the group consisting of talc, mica, silica, kaolin, polyamide powders, poly-β-alanine powders, polyethylene powders, powders of tetrafluoroethylene polymers, lauroyllysine, starch, boron nitride, hallow polymer microspheres, acrylic polymer particles, silicone resin microbeads, precipitated calcium carbonate, dicalcium phosphate, magnesium carbonate, magnesium hydrocarbonate, hydroxyapatite, hollow silica microspheres, glass, ceramic microcapsules, metal soaps derived from organic $C_8$–$C_{22}$ carboxylic acids, and mixtures thereof.

98. The process as claimed in claim 95, wherein the filler represents from 0.1% to 35% of the total weight of the first composition.

99. The process as claimed in claim 98, wherein the filler represents from 0.5% to 25% of the total weight of the first composition.

100. The process as claimed in claim 99, wherein the filler represents from 1% to 15% of the total weight of the first composition.

101. The process as claimed in claim 3, wherein the silicone-based and/or fluoro-based liquid phase of the second composition comprises a liquid phase that is nonvolatile at room temperature and atmospheric pressure.

102. The process as claimed in claim 101, wherein the nonvolatile liquid phase comprises at least one phenylsilicone oil.

103. The process as claimed in claim 102, wherein the phenylsilicone oil has a viscosity, measured at 25° C., ranging from 5 to 100,000 cSt.

104. The process as claimed in claim 103, wherein the phenylsilicone oil has a viscosity, measured at 25° C., ranging from 5 to 10,000 cSt.

105. The process as claimed in claim 102, wherein the silicone oil is selected from the group consisting of phenylsilicone oils of formula (A) below:

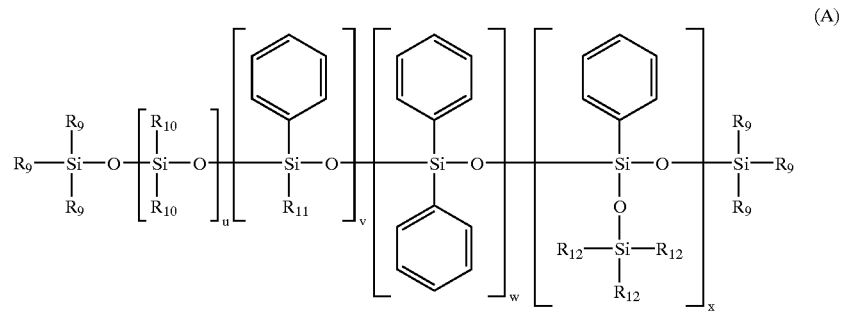

(A)

wherein
$R_9$ and $R_{12}$ are each independently a $C_1$–$C_{30}$-alkyl radical, an aryl radical or an aralkyl radical,
$R_{10}$ and $R_{11}$ are each independently a $C_1$–$C_{30}$-alkyl radical or an aralkyl radical,
u, v, w and x are each independently integers ranging from 0 to 900, with the proviso that the sum v+w+x is other than 0 and that the sum u+v+w+x ranges from 1 to 900.

106. The process as claimed hi claim 103, wherein the nonvolatile liquid phase comprises a low-viscosity phenylsilicone oil and a high-viscosity phenylsilicone oil.

107. The process as claimed in claim 106, wherein the low-viscosity phenylsilicone oil has a viscosity at 25° C. ranging from 5 to 499 cSt and the high-viscosity phenylsilicone oil has a viscosity at 25° C. ranging from 500 to 10,000 cSt.

108. The process as claimed in claim 107, wherein the low-viscosity phenylsilicone oil has a viscosity ranging from 5 to 300 cSt at 25° C. and the high-viscosity phenylsilicone oil has a viscosity ranging from 600 to 5,000 cSt at 25° C.

109. The process as claimed in claim 106, wherein the low-viscosity phenylsilicone oil satisfies formula (I) below:

(I)

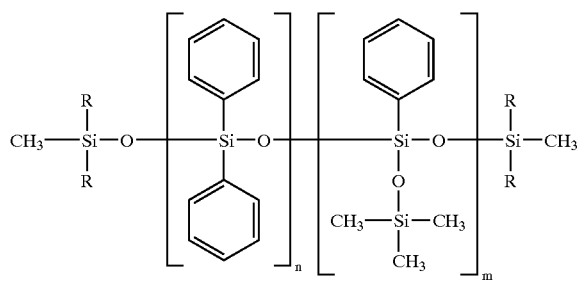

wherein

R is a $C_1$–$C_{30}$-alkyl radical, an aryl radical or an aralkyl radical, n is an integer ranging from 0 to 100, m is an integer ranging from 0 to 100, with the proviso that the sum m+n ranges from 1 to 100.

110. The process as claimed in claim 106, wherein the weight ratio of the low-viscosity phenylsilicone oil to the high-viscosity phenylsilicone oil ranges from 70/30 to 30/70.

111. The process as claimed in claim 110, wherein the weight ratio of the low-viscosity phenylsilicone oil to the high-viscosity phenylsilicone oil ranges from 60/40 to 40/60.

112. The process as claimed in claim 111, wherein the nonvolatile liquid phase comprises at least one fluoro compound selected from the group consisting of fluorosilicone compounds, fluoro polyethers and fluoroalkanes.

113. The process as claimed in claim 112, wherein the fluorosilicone compounds are selected from the group consisting of compounds of formula (II):

(II)

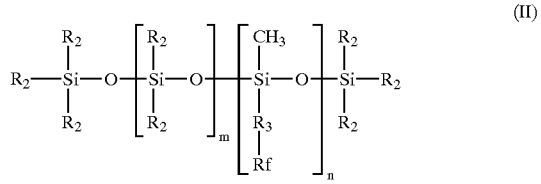

wherein:

$R_1$ represents a $C_1$–$C_6$ linear or branched divalent alkyl group,

Rf represents a $C_1$–$C_9$ fluoroalkyl radical, $R_2$ represent, independently of each other, a $C_1$–$C_{20}$ alkyl radical, a hydroxyl radical or a phenyl radical, m is a value from 0 to 150 and n is a value from 1 to 300.

114. The process as claimed in claim 112, wherein the fluoro polyethers are selected from the group consisting of compounds of formula (III):

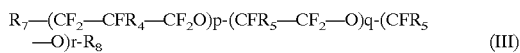

(III)

wherein:

$R_4$ to $R_7$ represent, independently of each other, a monovalent radical selected from the group consisting of —F, —($CF_2$)n-$CF_3$ and —O—($CF_2$)n-$CF_3$;

$R_8$ represents a monovalent radical selected from the group consisting of —F and —($CF_2$)n-$CF_3$;

with n ranging from 0 to 4; p ranging from 0 to 600, q ranging from 0 to 860, r ranging from 0 to 1,500, and p, q and r being integers selected such that the weight-average molecular weight of the compound ranges from 500 to 100,000.

115. The process as claimed in claim 112, wherein the fluoroalkanes are selected from the group consisting of $C_2$–$C_{50}$-perfluoroalkanes and fluoroalkanes.

116. The process as claimed in claim 3, wherein the silicone-based and/or fluoro-based liquid phase represents from 1% to 100% of the total weight of the second composition.

117. The process as claimed in claim 116, wherein the silicone-based and/or fluoro-based liquid phase represents from 5% to 95% of the total weight of the second composition.

118. The process as claimed in claim 3, wherein the physiological acceptable medium of the first and/or second composition contains a coloring agent.

119. The process as claimed in claim 117, wherein the coloring agent is selected from the group consisting of liposoluble dyes, water-soluble dyes, pigments, nacres, and mixtures thereof.

120. The process as claimed in claim 3, wherein the first composition comprises a coloring agent in the form of a dispersion.

121. The process as claimed in claim 118, wherein the coloring agent is present in an amount ranging from 0.001% to 60% of the total weight of the first or the second composition, respectively.

122. The process as claimed in claim 121, wherein the coloring agent is present in an amount ringing from 0.01% to 50% of the total weight of the first or the second composition, respectively.

123. The process as claimed in claim 3, wherein the physiologically acceptable medium for the first and/or second composition comprises one or more cosmetic or dermatological active agents.

124. The process as claimed in claim 123, wherein the physiologically acceptable medium for the first and/or second composition comprises a fatty substance selected from the group consisting of waxes, oils, gums and pasty fatty substances.

125. The process as claimed in claim 3, wherein the physiologically acceptable medium for the first composition comprises a gum.

126. The process as claimed in claim 125, wherein the gum is a silicone gum.

127. The process as claimed in claim 3, wherein the physiologically acceptable medium for the second composition comprises a pasty fatty substance and/or a wax.

128. The process as claimed in claim 3, wherein the physiologically acceptable medium for the first and/or second composition also comprises at least one additive selected from the group consisting of oil thickeners, aqueous-phase thickeners, antioxidants, fragrances, preserving agents, surfactants, liposoluble polymers, and mixtures thereof.

129. The process as claimed in claim 3, wherein the polymer particles are selected from the group consisting of polyurethanes, polyurethane-acrylics, polyureas, polyurea-polyurethanes, polyester-polyurethanes, polyether-polyurethanes, polyesters, polyesteramides, alkyl fatty-chain polyesters, acrylic polymers, acrylic copolymers, vinyl copolymers, vinyl polymers, acrylic-silicone copolymers, polyacrylamides, silicone polymers, fluoro polymers, and mixtures thereof.

130. The process as claimed in claim 3, wherein the stabilizer is selected from the group consisting of silicone polymers having a hydrocarbon-based chain graft, hydrocarbon-based polymers having a silicone chain graft, graft copolymers having an insoluble polyacrylic backbone with soluble grafts of poly(12-hydroxystearic acid), grafted-block copolymers comprising at least one polyorganosiloxane block and at least one block of a free-radical polymer, block copolymers comprising at least one polyorganosiloxane block and at least one block of a free-radical polymer, grafted-block copolymers comprising at least one polyorganosiloxane block and at least one block of a polyether, block copolymers comprising at least one polyorganosiloxane block and at least one block of a polyether, copolymers of $C_1$–$C_4$-alkyl acrylates, copolymers of $C_1$–$C_4$-alkyl methacrylates, copolymers of $C_8$–$C_{30}$ alkyl acrylates, copolymers of $C_8$–$C_{30}$ alkyl methacrylates, grafted-block copolymers comprising at least one block resulting from the polymerization of ethylenic monomers optionally comprising conjugated bonds and at least one block of a vinyl polymer, block copolymers comprising at least one block resulting from the polymerization of ethylenic monomers optionally comprising conjugated bonds and at least one block of a vinyl polymer, grafted-block comprising at least one block resulting from the polymerization of ethylenic monomers optionally comprising conjugated bonds and at least one block of an acrylic polymer, block copolymers comprising at least one block resulting from the polymerization of ethylenic monomers optionally comprising conjugated bonds and at least one block of an acrylic polymer, grafted-block copolymers comprising at least one block resulting from the polymerization of diene and at least one block of a polyether, block copolymers comprising at least one block resulting from the polymerization of diene and at least one block of a polyether, and mixtures thereof.

* * * * *

UNITED STATES PATENT AND TRADEMARK OFFICE
CERTIFICATE OF CORRECTION

PATENT NO. : 6,811,770 B2  
DATED : November 2, 2004  
INVENTOR(S) : Veronique Ferrari et al.

It is certified that error appears in the above-identified patent and that said Letters Patent is hereby corrected as shown below:

Title page,  
Item [75], Inventors, change "CAroline" to -- Caroline --.

Column 27,  
Line 35, change "baying" to -- having --.

Column 28,  
Line 21, change "structures" to -- thickens --.

Column 29,  
Line 30, change "10 000" to -- 10,000 --.

Column 33,  
Line 21, change "front" to -- from --.

Column 34,  
Line 54, change "hi" to -- in --.

Column 35,  
Line 46, change "$R_1$" to -- $R_3$ --; and  
Line 57, change "$CFR_5$" to -- $CFR_6$ --.

Signed and Sealed this

Second Day of August, 2005

JON W. DUDAS  
*Director of the United States Patent and Trademark Office*